(12) United States Patent
Stavens et al.

(10) Patent No.: US 7,423,103 B2
(45) Date of Patent: Sep. 9, 2008

(54) LOW FOULING AND HIGH ACTIVITY POLYMERIZATION PROCESS

(75) Inventors: Kevin B. Stavens, Seabrook, TX (US);
Robert O. Hagerty, La Porte, TX (US);
Randall B. Laird, Pasadena, TX (US);
Zerong Lin, Kingwood, TX (US);
Michael A. Risch, Seabrook, TX (US);
Larry L. Iaccino, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/629,502

(22) PCT Filed: Jun. 20, 2005

(86) PCT No.: PCT/US2005/021652

§ 371 (c)(1),
(2), (4) Date: Dec. 13, 2006

(87) PCT Pub. No.: WO2006/009949

PCT Pub. Date: Jan. 26, 2006

(65) Prior Publication Data

US 2007/0208154 A1     Sep. 6, 2007

Related U.S. Application Data

(60) Provisional application No. 60/581,595, filed on Jun. 21, 2004.

(51) Int. Cl.
*C08F 2/14*     (2006.01)
*C07C 17/38*   (2006.01)

(52) U.S. Cl. ............... 526/206; 526/74; 526/348.5; 526/348.6; 526/352; 526/912

(58) Field of Classification Search .......... 526/74, 526/206, 912, 348.5, 348.6, 352; 570/177, 570/178, 179
See application file for complete search history.

(56) References Cited

U.S. PATENT DOCUMENTS

| | | | |
|---|---|---|---|
| 2,534,698 A | 12/1950 | Calfee et al. | |
| 3,470,143 A | 9/1969 | Schrage et al. | |
| 4,194,073 A | 3/1980 | McDaniel | |
| 4,232,140 A | 11/1980 | Ort | |
| 4,510,342 A | 4/1985 | Currie et al. | |
| 4,588,790 A | 5/1986 | Jenkins, III et al. | |
| 5,087,329 A | 2/1992 | Felix | |
| 5,182,342 A * | 1/1993 | Feiring et al. | 526/206 |
| 5,352,749 A | 10/1994 | DeChellis et al. | |
| 5,405,922 A | 4/1995 | DeChellis et al. | |
| 5,556,821 A | 9/1996 | Aida et al. | |
| 5,728,641 A | 3/1998 | Aida et al. | |
| 5,780,565 A | 7/1998 | Clough et al. | |
| 2003/0027952 A1 | 2/2003 | Farrer et al. | |
| 2003/0157800 A1 | 8/2003 | Ohno et al. | |
| 2004/0015022 A1 | 1/2004 | Ohno et al. | |

FOREIGN PATENT DOCUMENTS

| | | |
|---|---|---|
| CN | 1 334 276 | 2/2002 |
| EP | 0 089 691 | 9/1983 |
| EP | 0 508 631 | 10/1992 |
| EP | 0 472 391 | 1/1996 |
| EP | 1 323 746 | 7/2003 |
| GB | 1 589 924 | 5/1981 |
| JP | 07304811 | 11/1995 |
| JP | 2001-139620 | 5/2001 |
| WO | WO00/75202 | 12/2000 |
| WO | WO02/053607 | 7/2002 |
| WO | WO02/055457 | 7/2002 |
| WO | WO03/010211 | 2/2003 |
| WO | WO2005/113610 | 12/2005 |
| WO | WO2005/113615 | 12/2005 |
| WO | WO2006/002132 | 1/2006 |
| WO | WO2006/009942 | 1/2006 |
| WO | WO2006/009944 | 1/2006 |
| WO | WO2006/009945 | 1/2006 |
| WO | WO2006/009946 | 1/2006 |
| WO | WO2006/009949 | 1/2006 |
| WO | WO2006/009951 | 1/2006 |
| WO | WO2006/009976 | 1/2006 |
| WO | WO2006/009977 | 1/2006 |
| WO | WO2006/009979 | 1/2006 |
| WO | WO2006/009980 | 1/2006 |
| WO | WO2006/009981 | 1/2006 |
| WO | WO2006/019494 | 2/2006 |
| WO | WO2006/025917 | 3/2006 |
| WO | WO2006/028549 | 3/2006 |
| WO | WO2006/083303 | 8/2006 |

OTHER PUBLICATIONS

U.S. Appl. No. 11/285,264, filed Nov. 22, 2005, Iaccino et al.
"A study of halocarbon promoter influence on catalyst reactivity and polymer Mn in vanadium-based ethylene polymerizations," Reinking, M. K. et al., Applied Catalysis A: General, Elsevier Science, Amsterdam, NL, vol. 189, No. 1, Nov. 22, 1999, 23-34, XP004272041.

* cited by examiner

*Primary Examiner*—Fred M Teskin
(74) *Attorney, Agent, or Firm*—Catherine L. Bell

(57) ABSTRACT

This invention is directed to a polymerization process that is carried out at relatively high productivity levels and with relatively low fouling. The process includes mixing together a catalyst system, at least one monomer and a hydrofluorocarbon to produce the polymer. The reaction is carried out such that little to no chlorine containing hydrocarbons are present.

43 Claims, No Drawings

US 7,423,103 B2

LOW FOULING AND HIGH ACTIVITY POLYMERIZATION PROCESS

PRIORITY CLAIM

This application is the national phase entry into the United States Patent Office of international application number PCT/US2005/021652 filed Jun. 20, 2005, which claims benefit of and priority to United States Provisional Patent Application Ser. No. 60/581,595 filed Jun. 21, 2004.

FIELD OF THE INVENTION

This invention relates to a low fouling, high activity polymerization process. More specifically, this invention relates to a low fouling, high activity polymerization process that incorporates the use of hydrofluorocarbon diluent containing little to no chlorine containing hydrocarbons.

BACKGROUND OF THE INVENTION

Polymerization generally involves polymerization of one or more monomers to make a polymeric product. The polymerization reaction can be carried out using a wide variety of reactors, catalysts, and a wide variety of monomer feeds. Often, liquids, diluents or solvents are used in these polymerization reaction processes for various reasons such as to increase the efficiency of the polymerization reaction and recovery of polymer product.

An example of a polymerization process that incorporates the use of a hydrocarbon diluent is shown in U.S. Pat. No. 3,470,143 (Schrage et al.). Specifically, the Schrage patent discloses a laboratory scale polymerization reaction that incorporates the use of an organic fluorinated carbon compound as the diluent.

There are needs for improved polymerization processes, for example reducing reactor fouling at commercial scale, enhancing the commercial grade slate of polymer products produced from a given process, increasing polymer production capacity without significant investment where these process improvements necessitate more efficient recovery systems that provide environmental benefits as well as cost reductions. In particular, there is a need for increasing polymerization catalyst activity, while maintaining a low degree of reactor fouling, and for producing a wide grade of commercial polymer products.

SUMMARY OF THE INVENTION

The invention provides a process for making a polymer product at relatively high catalytic productivity and with very low reactor fouling during the reaction process. The invention incorporates the use of a hydrofluorocarbon compound, and the compound as well as the reaction system has little to no chlorine containing hydrocarbon compounds.

According to one aspect of the invention, there is provided a polymerization process that comprises mixing together a catalyst system, at least one monomer and a hydrofluorocarbon to produce a polymer. The mixture in which the polymer is produced should contain no single chlorine containing hydrocarbon compound at greater than 40 ppma, preferably greater than 30 ppma, more preferably greater than 25 ppma, and most preferably greater than 20 ppma.

In one aspect of the invention, the polymerization process comprises mixing together a catalyst system, at least one monomer and a hydrofluorocarbon, and forming the polymer in the presence of not greater than 40 ppma of any single chlorine containing hydrocarbon compound. Preferably, the polymer is formed in the presence of not greater than 30 ppma, more preferably not greater than 25 ppma, and most preferably not greater than 20 ppma of any single chlorine containing hydrocarbon compound.

In another embodiment of the invention, the polymerization process includes removing chlorine containing hydrocarbons from a mixture containing hydrofluorocarbon to produce a hydrofluorocarbon product containing no single chlorine containing hydrocarbon compound in a amount that would significantly adversely inhibit polymer catalyst activity. The hydrocarbon product is mixed with at least one monomer and a catalyst system to produce a polymer.

In another embodiment of the invention, the polymerization process includes removing chlorine containing hydrocarbons from a mixture containing hydrofluorocarbon to produce a hydrofluorocarbon product. The hydrocarbon product is mixed with at least one monomer and a catalyst system to form a polymer at a productivity of at least 400 g/g/hr, preferably at least 500 g/g/hr, more preferably at least 600 g/g/hr, still more preferably at least 700 g/g/hr, and most preferably at least 800 g/g/hr.

In yet another embodiment, the process comprises removing chlorine containing hydrocarbons from a mixture containing hydrofluorocarbon to produce a hydrofluorocarbon product, and mixing the hydrocarbon product with at least one monomer and a catalyst system to form a polymer at a polymer fouling of not greater than 5 wt %. Preferably, the polymer is formed at a polymer fouling of not greater than 4 wt %, more preferably not greater than 3 wt %, still more preferably not greater than 2 wt %, and most preferably not greater than 1 wt %.

In one embodiment, the hydrofluorocarbon used in the process is represented by the formula: $C_xH_yF_z$ wherein x is an integer from 1 to 40, y is greater than or equal to 0, and z is an integer and at least one.

In general, the chlorine containing hydrocarbon compounds that are referred to in this invention are represented by the formula: $Cl_aF_bC_cH_d$, wherein a is an integer of from 1 to 14, b is an integer of from 1 to 13, c is an integer of from 1 to 6, and d is an integer of from 0 to 13. Particularly problematic chlorine containing hydrocarbon compounds are one or more compounds selected from the group consisting of: trichlorofluoromethane, hexafluorochloropropane, chlorotetrafluoropropene, chlorotrifluoropropene, 1,1-dichloro-2,2-difluoroethene, and pentafluoro-2-chloropropene.

In one embodiment, the at least one monomomer includes one or more of ethylene, propylene, butene-1, pentene-1,4-methyl-pentene-1, hexene-1, octene-1, decene-1,3-methyl-pentene-1, norbornene, norbornadiene, 3,5,5-trimethyl-1-hexene, 5-ethyl-1-nonene, vinyl norbornene, and ethylidene monomers.

In another embodiment, one or more of the chlorine containing hydrocarbon compounds are removed from a mixture containing the hydrofluorocarbon prior to producing the polymer. Generally, the mixture contains a total amount of chlorine containing hydrocarbons of 50,000 ppm or less, by mass. Preferably, the one or more chlorine containing compounds are removed by one or more processes selected from the group consisting of distillation, extractive distillation, contacting with metal permanganate, contacting with chromium oxide, adsorption, reactive distillation, and contacting with one or more decomposing agents.

DETAILED DESCRIPTION OF THE INVENTION

I. Introduction

This invention is directed to a polymerization process that is carried out at relatively high productivity levels and with relatively low fouling. The process includes mixing together a catalyst system, at least one monomer and a hydrofluorocarbon to produce the polymer. The reaction is carried out such that little to no chlorine containing hydrocarbons are present.

The inventors have found that polymerization processes that include hydrofluorocarbon as a diluent material in a polymerization reaction mixture are negatively impacted in cases where the reaction is carried out in the presence of even small amounts of chlorine containing hydrocarbons. Typically, the presence of even low levels of such chlorine containing compounds negatively impact productivity. At commercial scale production, low levels of productivity loss can be quite substantial, resulting in many cases as a substantial loss in reactor production capacity.

II. HFC Diluent Material

The diluents used in this invention are beneficial in producing highly useful polymer products. Use of the diluents can also provide polymer processes having reduced fouling, higher overall efficiencies and/or reduced environmental emissions. The diluents of the invention are preferably compositions added to the reaction process that reduce the concentration of one or more active materials in the process to achieve the desired and beneficial effect. Preferably, the diluent is a hydrocarbon having little to no solvent power. More preferably, the diluent is a halogen containing, most preferably fluorinated hydrocarbon, compound, and preferably having little to no solvent power with respect to the polymer product. The fluorinated hydrocarbons may be used individually or as mixtures, and can be included in a mixture with non-fluorinated hydrocarbon diluents if desired.

According to this invention, fluorinated hydrocarbons are interchangeably referred to as hydrofluorocarbons or hydrofluorocarbon compounds or HFCs. These compounds have at least one carbon atom and at least one fluorine atom. The fluorinated hydrocarbon can be a perfluorinated hydrocarbon or the fluorinated hydrocarbon can optionally include one or more hydrogen atom(s). A perfluorinated hydrocarbon is a fluorocarbon in which the hydrogen directly attached to the carbon atom(s) is completely replaced by fluorine. See *Hawley's Condensed Chemical Dictionary*, Thirteenth Edition, Van Nostrand Renhold, 1997. Examples of preferred perfluorocarbons include linear branched or cyclic, $C_1$ to $C_{40}$ perfluoroalkanes.

In one embodiment, the fluorinated hydrocarbons are represented by the formula:

$$C_xH_yF_z$$

wherein x is an integer from 1 to 40, alternatively from 1 to 30, alternatively from 1 to 20, alternatively from 1 to 10, alternatively from 1 to 6, alternatively from 2 to 20 alternatively from 3 to 10, alternatively from 3 to 6, most preferably from 1 to 3, wherein y is greater than or equal to 0 and z is an integer and at least one, more preferably, y and z are integers and at least one. In a preferred embodiment, z is 2 or more.

In one embodiment, a mixture of fluorinated hydrocarbons are used in the process of the invention, preferably a mixture of a perfluorinated hydrocarbon and a fluorinated hydrocarbon, and more preferably a mixture of a fluorinated hydrocarbon. In yet another embodiment, the fluorinated hydrocarbon is balanced or unbalanced in the number of fluorine atoms in the fluorinated hydrocarbon compound.

Non-limiting examples of fluorinated hydrocarbons include fluoromethane; difluoromethane; trifluoromethane; fluoroethane; 1,1-difluoroethane; 1,2-difluoroethane; 1,1,1-trifluoroethane; 1,1,2-trifluoroethane; 1,1,1,2-tetrafluoroethane; 1,1,2,2-tetrafluoroethane; 1,1,1,2,2-pentafluoroethane; 1-fluoropropane; 2-fluoropropane; 1,1-difluoropropane; 1,2-difluoropropane; 1,3-difluoropropane; 2,2-difluoropropane; 1,1,1-trifluoropropane; 1,1,2-trifluoropropane; 1,1,3-trifluoropropane; 1,2,2-trifluoropropane; 1,2,3-trifluoropropane; 1,1,1,2-tetrafluoropropane; 1,1,1,3-tetrafluoropropane; 1,1,2,2-tetrafluoropropane; 1,1,2,3-tetrafluoropropane; 1,1,3,3-tetrafluoropropane; 1,2,2,3-tetrafluoropropane; 1,1,1,2,2-pentafluoropropane; 1,1,1,2,3-pentafluoropropane; 1,1,1,3,3-pentafluoropropane; 1,1,2,2,3-pentafluoropropane; 1,1,2,3,3-pentafluoropropane; 1,1,1,2,2,3-hexafluoropropane; 1,1,1,2,3,3-hexafluoropropane; 1,1,1,3,3,3-hexafluoropropane; 1,1,1,2,2,3,3-heptafluoropropane; 1,1,1,2,3,3,3-heptafluoropropane; 1-fluorobutane; 2-fluorobutane; 1,1-difluorobutane; 1,2-difluorobutane; 1,3-difluorobutane; 1,4-difluorobutane; 2,2-difluorobutane; 2,3-difluorobutane; 1,1,1-trifluorobutane; 1,1,2-trifluorobutane; 1,1,3-trifluorobutane; 1,1,4-trifluorobutane; 1,2,2-trifluorobutane; 1,2,3-trifluorobutane; 1,3,3-trifluorobutane; 2,2,3-trifluorobutane; 1,1,1,2-tetrafluorobutane; 1,1,1,3-tetrafluorobutane; 1,1,1,4-tetrafluorobutane; 1,1,2,2-tetrafluorobutane; 1,1,2,3-tetrafluorobutane; 1,1,2,4-tetrafluorobutane; 1,1,3,3-tetrafluorobutane; 1,1,3,4-tetrafluorobutane; 1,1,4,4-tetrafluorobutane; 1,2,2,3-tetrafluorobutane; 1,2,2,4-tetrafluorobutane; 1,2,3,3-tetrafluorobutane; 1,2,3,4-tetrafluorobutane; 2,2,3,3-tetrafluorobutane; 1,1,1,2,2-pentafluorobutane; 1,1,1,2,3-pentafluorobutane; 1,1,1,2,4-pentafluorobutane; 1,1,1,3,3-pentafluorobutane; 1,1,1,3,4-pentafluorobutane; 1,1,1,4,4-pentafluorobutane; 1,1,2,2,3-pentafluorobutane; 1,1,2,2,4-pentafluorobutane; 1,1,2,3,3-pentafluorobutane; 1,1,2,4,4-pentafluorobutane; 1,1,3,3,4-pentafluorobutane; 1,2,2,3,3-pentafluorobutane; 1,2,2,3,4-pentafluorobutane; 1,1,1,2,2,3-hexafluorobutane; 1,1,1,2,2,4-hexafluorobutane; 1,1,1,2,3,3-hexafluorobutane, 1,1,1,2,3,4-hexafluorobutane; 1,1,1,2,4,4-hexafluorobutane; 1,1,1,3,3,4-hexafluorobutane; 1,1,1,3,4,4-hexafluorobutane; 1,1,1,4,4,4-hexafluorobutane; 1,1,2,2,3,3-hexafluorobutane; 1,1,2,2,3,4-hexafluorobutane; 1,1,2,2,4,4-hexafluorobutane; 1,1,2,3,3,4-hexafluorobutane; 1,1,2,3,4,4-hexafluorobutane; 1,2,2,3,3,4-hexafluorobutane; 1,1,1,2,2,3,3-heptafluorobutane; 1,1,1,2,2,4,4-heptafluorobutane; 1,1,1,2,2,3,4-heptafluorobutane; 1,1,1,2,3,3,4-heptafluorobutane; 1,1,1,2,3,4,4-heptafluorobutane; 1,1,1,2,4,4,4-heptafluorobutane; 1,1,1,3,3,4,4-heptafluorobutane; 1,1,1,2,2,3,3,4-octafluorobutane; 1,1,1,2,2,3,4,4-octafluorobutane; 1,1,1,2,3,3,4,4-octafluorobutane; 1,1,1,2,2,4,4,4-octafluorobutane; 1,1,1,2,3,4,4,4-octafluorobutane; 1,1,1,2,2,3,3,4,4-nonafluorobutane; 1,1,1,2,2,3,4,4,4-nonafluorobutane; 1-fluoro-2-methylpropane; 1,1-difluoro-2-methylpropane; 1,3-difluoro-2-methylpropane; 1,1,1-trifluoro-2-methylpropane; 1,1,3-trifluoro-2-methylpropane; 1,3-difluoro-2-(fluoromethyl)propane; 1,1,1,3-tetrafluoro-2-methylpropane; 1,1,3,3-tetrafluoro-2-methylpropane; 1,1,3-trifluoro-2-(fluoromethyl)propane; 1,1,1,3,3-pentafluoro-2-methylpropane; 1,1,3,3-tetrafluoro-2-(fluoromethyl)propane; 1,1,1,3-tetrafluoro-2-(fluoromethyl)propane; fluorocyclobutane; 1,1-difluorocyclobutane; 1,2-difluorocyclobutane; 1,3-difluorocyclobutane; 1,1,2-trifluorocyclobutane; 1,1,3-trifluorocyclobutane; 1,2,3-trifluorocyclobutane; 1,1,2,2-tetrafluorocyclobutane; 1,1,3,3-tetrafluorocyclobutane; 1,1,2,2,3-pentafluorocyclobutane; 1,1,2,3,3-pentafluorocyclobutane; 1,1,2,2,3,3-hexafluorocyclobutane; 1,1,2,2,3, 4-hexafluorocyclobutane; 1,1,2,3,3,4-hexafluorocyclobutane; 1,1,2,2,3,3,4-heptafluorocyclobutane. Particularly preferred fluorinated hydrocarbons include difluoromethane, trifluoromethane, 1,1-difluoroethane, 1,1,1-trifluoroethane, fluoromethane, and 1,1,1,2-tetrafluoroethane. In addition to those fluorinated hydrocarbons described herein, those fluorinated hydrocarbons described in Raymond Will, et. al., CEH Marketing Report, Fluorocarbons, Pages 1-133, by the Chemical Economics Handbook—SRI International, April 2001, which is fully incorporated herein by reference, are included.

In another embodiment the fluorinated hydrocarbons are used in combination with one or more inert gases such as carbon dioxide, nitrogen, argon, neon, helium, krypton, zenon, and the like. In the preferred embodiment, the inert gas is nitrogen.

In another preferred embodiment, the fluorinated hydrocarbon used in the process of the invention are selected from the group consisting of difluoromethane, trifluoromethane, 1,1-difluoroethane, 1,1,1-trifluoroethane, and 1,1,1,2-tetrafluoroethane and mixtures thereof.

In one particularly preferred embodiment, the commercially available fluorinated hydrocarbons useful in the process of the invention include HFC-236fa having the chemical name 1,1,1,3,3,3-hexafluoropropane, HFC-134a having the chemical name 1,1,1,2-tetrafluoroethane, HFC-245fa having the chemical name 1,1,1,3,3-pentafluoropropane, HFC-365mfc having the chemical name 1,1,1,3-pentafluorobutane, R-318 having the chemical name octafluorocyclobutane, and HFC-43-10mee having the chemical name 2,3-dihydrodecafluoropentane, all of these are commercially available fluorinated hydrocarbons.

In another embodiment, the fluorocarbon is not a perfluorinated C4 to C10 alkane. In another embodiment, the fluorocarbon is not a perfluorinated hydrocarbon. In another embodiment, the fluorocarbon is not perfluorodecalin, perfluoroheptane, perfluorohexane, perfluoromethylcyclohexane, perfluorooctane, perfluoro-1,3-dimethylcyclohexane, perfluorononane, fluorobenzene, or perfluorotoluene. In a particularly preferred embodiment, the fluorocarbon consists essentially of hydrofluorocarbons.

In another embodiment the fluorocarbon is present at more than 1 weight %, based upon the weight of the fluorocarbon and any hydrocarbon solvent present in the reactor, preferably greater than 3 weight %, preferably greater than 5 weight %, preferably greater than 7 weight %, preferably greater than 10 weight %, preferably greater than 15 weight %, preferably greater than 20 weight %, preferably greater than 25 weight %, preferably greater than 30 weight %, preferably greater than 35 weight %, preferably greater than 40 weight %, preferably greater than 50 weight %, preferably greater than 55 weight %, preferably greater than 60 weight %, preferably greater than 70 weight %, preferably greater than 80 weight %, preferably greater than 90 weight %. In another embodiment the fluorocarbon is present at more than 1 weight %, based upon the weight of the fluorocarbons, monomers and any hydrocarbon solvent present in the reactor, preferably greater than 3 weight %, preferably greater than 5 weight %, preferably greater than 7 weight %, preferably greater than 10 weight %, preferably greater than 15 weight %, preferably greater than 20 weight %, preferably greater than 25 weight %, preferably greater than 30 weight %, preferably greater than 35 weight %, preferably greater than 40 weight %, preferably greater than 50 weight %, preferably greater than 55 weight %, preferably greater than 60 weight %, preferably greater than 70 weight %, preferably greater than 80 weight %, preferably greater than 90 weight %. In the event that the weight basis is not named for the weight % fluorocarbon, it shall be presumed to be based upon the total weight of the fluorocarbons, monomers and hydrocarbon solvents present in the reactor.

In another embodiment the fluorocarbon, preferably the hydrofluorocarbon, is present at more than 1 volume %, based upon the total volume of the fluorocarbon and any hydrocarbon solvent present in the reactor, preferably greater than 3 volume %, preferably greater than 5 volume %, preferably greater than 7 volume %, preferably greater than 10 volume %, preferably greater than 15 volume %, preferably greater than 20 volume %, preferably greater than 25 volume %, preferably greater than 30 volume %, preferably greater than 35 volume %, preferably greater than 40 volume %, preferably greater than 45 volume %, preferably greater than 50 volume %, preferably greater than 55 volume %, preferably greater than 60 volume %, preferably greater than 65 volume %. Alternatively, at least 5 volume % of the hydrofluorocarbon is present, based upon the total volume of the diluent.

In another embodiment the fluorocarbon is a blend of hydrofluorocarbon and perfluorocarbon and preferably the hydrofluorocarbon is present at more than 1 volume %, based upon the total volume of the perfluorocarbon and the hydrofluorocarbon present in the reactor, (with the balance being made up by the perfluorocarbon) preferably greater than 3 volume %, preferably greater than 5 volume %, preferably greater than 7 volume %, preferably greater than 10 volume %, preferably greater than 15 volume %, preferably greater than 20 volume %, preferably greater than 25 volume %, preferably greater than 30 volume %, preferably greater than 35 volume %, preferably greater than 40 volume %, preferably greater than 45 volume %, preferably greater than 50 volume %, preferably greater than 55 volume %, preferably greater than 60 volume %, preferably greater than 65 volume %.

In yet another embodiment, the fluorinated hydrocarbons of the invention have a molecular weight (MW) greater than 90 a.m.u., preferably greater than 95 a.m.u, and more preferably greater than 100 a.m.u. In another embodiment, the fluorinated hydrocarbons of the invention have a MW greater than 120 a.m.u, preferably greater than 125 a.m.u, even more preferably greater than 130 a.m.u, and most preferably greater than 140 a.m.u. In still another embodiment, the fluorinated hydrocarbons of the invention have a MW greater than 125 a.m.u, preferably greater than 130 a.m.u, even more preferably greater than 135 a.m.u, and most preferably greater than 150 a.m.u. In another embodiment, the fluorinated hydrocarbons of the invention have a MW greater than 140 a.m.u, preferably greater than 150 a.m.u, more preferably greater than 180 a.m.u, even more preferably greater than 200 a.m.u, and most preferably greater than 225 a.m.u. In an embodiment, the fluorinated hydrocarbons of the invention have a MW in the range of from 90 a.m.u to 1000 a.m.u, preferably in the range of from 100 a.m.u to 500 a.m.u, more preferably in the range of from 100 a.m.u to 300 a.m.u, and most preferably in the range of from about 100 a.m.u to about 250 a.m.u.

In yet another embodiment, the fluorinated hydrocarbons of the invention have normal boiling point in the range of from about −50° C. up to the polymerization temperature, preferably a polymerization temperature of about 85° C., preferably the normal boiling point of the fluorinated hydrocarbons is in the range of from −40° C. to about 70° C., more preferably from about −130° C. to about 60° C., and most preferably from about −30° C. to about 55° C. In an embodiment, the fluorinated hydrocarbons of the invention have normal boiling point greater than −30° C., preferably greater than −30° C.

to less than −10° C. In a further embodiment, the fluorinated hydrocarbons of the invention have normal boiling point greater than −5° C., preferably greater than −5° C. to less than −20° C. In one embodiment, the fluorinated hydrocarbons of the invention have normal boiling point greater than 30° C., preferably greater than 30° C. to about 60° C.

In another embodiment, the fluorinated hydrocarbons of the invention have a liquid density @20° C. (g/cc) greater than 1 g/cc, preferably greater than 1.10, and most preferably greater than 1.20 g/cc. In one embodiment, the fluorinated hydrocarbons of the invention have a liquid density@20° C. (g/cc) greater than 1.20 g/cc, preferably greater than 1.25, and most preferably greater than 1.30 g/cc. In one embodiment, the fluorinated hydrocarbons of the invention have a liquid Density @20° C. (g/cc) greater than 1.30 g/cc, preferably greater than 1.40, and most preferably greater than 1.50 g/cc.

In one embodiment, the fluorinated hydrocarbons of the invention have a ΔH Vaporization as measured by standard calorimetry techniques in the range between 100 kJ/kg to less than 300 kJ/kg, preferably in the range of from 110 kJ/kg to less than 300 kJ/kg, and most preferably in the range of from 120 kJ/kg to less than 300 kJ/kg.

In another preferred embodiment, the fluorinated hydrocarbons of the invention comprises any combination of two or more of the aforementioned MW, normal boiling point, ΔH Vaporization, and liquid density values and ranges. In a preferred embodiment, the fluorinated hydrocarbons useful in the process of the invention have a MW greater than 90 a.m.u, preferably greater than 100 a.m.u, and a liquid density greater than 1.00 g/cc, preferably greater than 1.20 g/cc. In yet another preferred embodiment, the fluorinated hydrocarbons useful in the process of the invention have a liquid density (at 20° C.) greater than 1.10 g/cc, preferably greater than 1.20 g/cc, and a normal boiling point greater than −50° C., preferably greater than −30° C. up to the polymerization temperature of the process, which is as high as 100° C., preferably less than 85° C., and more preferably less than 75° C., and most preferably less than 60° C. In one embodiment, the fluorinated hydrocarbons useful in the process of the invention have a MW greater than 90 a.m.u, preferably greater than 100 a.m.u, and a ΔH Vaporization in the range of from 100 kj/kg to less than 300 kj/kg, and optionally a liquid density greater than 1.00 g/cc, preferably greater than 1.20 g/cc. In yet another embodiment, the fluorinated hydrocarbons useful in the process of the invention have a liquid density greater than 1.10 g/cc, preferably greater than 1.20 g/cc, and a normal boiling point greater than −50° C., preferably greater than −30° C. up to the polymerization temperature of the process, which is as high as 100° C., preferably less than 85° C., and more preferably less than 75° C., and most preferably less than 60° C., and optionally a ΔH Vaporization in the range of from 120 kj/kg to less than 250 kj/kg.

In yet another embodiment, the diluent includes one or more fluorinated hydrocarbon(s) alone or in combination with one or more inert condensable agent(s) or condensing agent(s). Examples of suitable, preferably inert, condensable agents include volatile liquid hydrocarbons, for example, saturated hydrocarbons containing from 1 to 10, preferably 3 to 8, carbon atoms. Preferred examples include propane, n-butane, isobutane (MW of 58.12 a.m.u, a liquid density of 0.55 g/cc, and normal boiling point as above described of −11.75), n-pentane, isopentane (MW of 72.15 a.m.u, a liquid density of 0.62 g/cc, and normal boiling point of 27.85), neopentane, n-hexane, isohexane, and other saturated $C_4$ to $C_8$ hydrocarbons. In one embodiment, the diluent further comprises at least one $C_1$ to $C_8$ alkane.

In another embodiment, the diluent material, which contains the hydrofluorocarbon as well as the other optional condensable fluid, is selected based upon its solubility or lack thereof in a particular polymer being produced. Preferred diluents have little to no solubility in the polymer. Solubility in the polymer is measured by forming the polymer into a film of thickness between 50 and 100 microns, then soaking it in diluent (enough to cover the film) for 4 hours at the relevant desired temperature in a sealed container or vessel. The film is removed from the diluent, exposed for 90 seconds to evaporate excess fluid from the surface of the film, and weighed. The mass uptake is defined as the percentage increase in the film weight after soaking. The diluent is preferably selected so that the polymer has a mass uptake of less than 4 wt %, preferably less than 3 wt %, more preferably less than 2 wt %, even more preferably less than 1 wt %, and most preferably less than 0.5 wt %.

In a preferred embodiment, the diluent, preferably the fluorinated hydrocarbon(s) or mixtures thereof, are selected such that the polymer melting temperature Tm is reduced (or depressed) by not more than 15° C. by the presence of the condensable fluid. The depression of the polymer melting temperature ΔTm is determined by first measuring the melting temperature of a polymer by differential scanning calorimetry (DSC), and then comparing this to a similar measurement on a sample of the same polymer that has been soaked with the condensable fluid. In general, the melting temperature of the soaked polymer will be lower than that of the dry polymer. The difference in these measurements is taken as the melting point depression ΔTm. It is well known to those in the art that higher concentrations of dissolved materials in the polymer cause larger depressions in the polymer melting temperature (i.e. higher values of AΔm). A suitable DSC technique for determining the melting point depression is described by, P. V. Hemmingsen, "Phase Equilibria in Polyethylene Systems", Ph.D. Thesis, Norwegian University of Science and Technology, March 2000, which is incorporated herein by reference. (A preferred set of conditions for conducting the tests are summarized on Page 112 of this reference.) The polymer melting temperature is first measured with dry polymer, and then repeated with the polymer immersed in liquid (the condensable fluid to be evaluated). As described in the reference above, it is important to ensure that the second part of the test, conducted in the presence of the liquid, is done in a sealed container so that the liquid is not flashed during the test, which could introduce experimental error. In one embodiment, the ΔTm is less than 12° C., preferably less than 10° C., preferably less than 8° C., more preferably less than 6° C., and most preferably less than 4° C. In another embodiment, the measured ΔTm is less than 5° C., preferably less than 4° C., more preferably less than 3° C., even more preferably less than 2° C., and most preferably less than 1° C.

In another embodiment, the fluorinated hydrocarbon is present in the diluent at greater than 5 wt %, based on the total weight of the diluent. Preferably the fluorinated hydrocarbon is present in the diluent at greater than 7 wt %, more preferably greater than 10 wt %, and most preferably greater than 15 wt %, based on the total weight of the diluent. In another embodiment, the fluorinated hydrocarbon is present in the diluent at not greater than 90 wt %, based on the total weight of the diluent. Preferably the fluorinated hydrocarbon is present in the diluent at not greater than 80 wt %, more preferably not greater than 70 wt %, still more preferably not greater than 60 wt %, and most preferably not greater than 50 wt %, based on the total weight of the diluent. In yet another embodiment, the fluorinated hydrocarbon in the diluent is not a perfluorinated $C_4$ to $C_{10}$ alkane.

III. Chlorine Containing Hydrocarbons

The HFC diluent material used in the polymerization process of this invention contains little to no chlorine containing hydrocarbon compounds that would substantially inhibit or reduce polymerization productivity. The presence of even small levels of various chlorine containing compounds can cause a substantial reduction in polymer productivity. Therefore, the HFC diluent material used should be of appropriate or predetermined purity when used in the polymerization process or at least be reduced or adsorbed during the process to a level that has no substantial effect on polymer productivity.

Various chlorine containing hydrocarbons have different effects on various catalysts. For example, one chlorine containing hydrocarbon may have a lesser effect on one catalyst than another type of catalyst. According to a preferred embodiment this invention, the level of any specific chlorine containing compound should not be so high as to substantially reduce polymer productivity and/or to substantially increase reactor fouling.

In one embodiment of the invention, the polymerization process is carried out at a low level of chlorine containing hydrocarbon and at a productivity of at least 400 g/g/hr, where g/g/hr is grams of polymer produced per gram of catalyst used in the process per hour of polymerization time. Preferably, the polymerization process is carried out at a productivity of at least 500 g/g/hr, more preferably at least 600 g/g/hr, still more preferably at least 700 g/g/hr, and most preferably at least 800 g/g/hr.

In another embodiment of the invention, the polymerization process is carried out with low or no reactor fouling. In one embodiment, the polymerization process is carried out at a reactor fouling of not greater than 5 wt %. The weight percent fouling is determined by scraping or otherwise removing all polymer foulant from the walls of the reactor, and dividing this weight by the total weight of polymer in the reactor (normal polymer plus the foulant material). Preferably, the polymerization process is carried out at a reactor fouling of not greater than 4 wt %, more preferably not greater than 3 wt %, still more preferably not greater than 2 wt %, and most preferably not greater than 1 wt %.

The amount of chlorine containing hydrocarbon is preferably determined using appropriate gas chromatography/mass selective detector (GC/MSD) analysis. For example, the GC/MSD analysis can be carried out using a HP6890 GC/MSD or equivalent device. According to one embodiment of the invention, the amount of chlorine containing hydrocarbon present is determined on the basis of part per million area (ppma). The ppma is the area value of any given peak relative to the total area for that analysis. For example, if a single peak representing one compound measures a peak area of 0.01% of the total GC/MSD peak area for a particular analysis, then the concentration of that compound would be 100 ppma.

In one embodiment, chlorine containing hydrocarbons are removed from a mixture containing hydrofluorocarbon to produce a hydrocarbon product containing no single chlorine containing hydrocarbon compound above the desired or predetermined limit. In another embodiment, a mixture containing hydrofluorocarbon and one or more chlorine containing hydrocarbons is mixed with a catalyst system and one or more polymers and the chlorine containing compound or compounds are adsorbed so as not to substantially impact polymer productivity. For example, chromium oxide type catalysts can be used as chlorine compound adsorbent as well as polymer catalyst.

In one embodiment the, chlorine containing hydrocarbon compounds that are referred to in this invention are represented by the formula:

wherein a is an integer of from 1 to 14, b is an integer of from 1 to 13, c is an integer of from 1 to 6, and d is an integer of from 0 to 13. In a more particular embodiment, a is an integer of from 1 to 8, b is an integer of from 0 to 7, c is 2 or 3, and d is an integer of from 0 to 7. More particularly, a is an integer of from 1 to 5, b is an integer of from 0 to 6, c is 2 or 3, and d is an integer of from 1 to 7.

Exemplary chlorine containing hydrocarbon compounds include chloromethane; dichloromethane; chloroform; carbon tetrachloride; chlorofluoromethane; chlorodifluoromethane; fluorodichloromethane; chlorotrifluoromethane; fluorotrichloromethane; chloroethane; 1,1-dichloroethane; 1,2-dichloroethane; 1-chloro-1-fluoroethane; 1-chloro-2-fluoroethane; 1,1,1-trichloroethane; 1,1,2-trichloroethane; 1-chloro-1,1-difluoroethane; 1-fluoro-1,1-dichloroethane; 1-chloro-1,2-difluoroethane; 1-fluoro-1,2-dichloroethane; 2-chloro-1,1-difluoroethane; 2-fluoro-1,1-dichloroethane; 1,1,1,2-tetrachloroethane; 1,1,2,2-tetrachloroethane; 2-chloro-1,1,1-trifluoroethane; 2-fluoro-1,1,1-trichloroethane; 1,1-dichloro-2,2-difluoroethane; 1,2-dichloro-1,2-difluoroethane; hexachloroethane; chloropentafluoroethane; chloroethylene; 1,1-dichloroethylene; 1,1,2-trichloroethylene; 1,1,2,2-tetrachloroethylene; 1-chloro-1,2,2-trifluoroethylene; 1,1-dichloro-2,2-difluoroethylene; 1,2-dichloro-1,2-difluoroethylene; 1-chloropropane; 2-chloropropane; 1,3-dichloropropane; 1-chlorobutane; 2-chlorobutane; 1-chloro-2-methylpropane; 2-chloro-2-methylpropane; 1-chloropentane; 2-chloropentane; 3-chloropentane; chloro-2-methyl-butane; 1-chloro-3-methyl-butane; 2-chloro-2-methyl-butane; 1-chloro-2,2-dimethylpropane; perfluoropropyl chloride; perfluoroisopropyl chloride and the like.

Exemplary alicyclic chlorine containing hydrocarbon compounds include chlorocyclopropane, hexachlorocyclopentadiene, pentachlorocyclopropane; chlorocyclobutane; chlorocyclopentane; chlorocyclohexane; 1,1-dichlorocyclobutane; 1,1-dichlorocyclopentane; 1,1-dichlorocyclohexane; cis-1,2-dichlorocyclobutane; cis-1,2-dichlorocyclopentane; cis-1,2-dichlorocyclohexane; trans-1,2-dichlorocyclobutane; trans-1,2-dichlorocyclopentane, trans-1,2-dichlorocyclohexane; alpha-1,2,3,4,5,6-hexachlorocyclohexane; tetrachlorocyclopropene and the like.

Exemplary aromatic chlorine containing hydrocarbon compounds include chlorobenzene; 1,2-dichlorobenzene; 1,3-dichlorobenzene; 1,4-dichlorobenzene; 1-chloro-2-fluorobenzene; 1-chloro-3-fluorobenzene; 1-chloro-4-fluorobenzene; 1,2,3-trichlorobenzene; 1,2,4-trichlorobenzene; 1,2,3,4-tetrachlorobenzene; 1,2,3,5-tetrachlorobenzene; pentachlorobenzene; hexachlorobenzene; benzyl chloride; alpha,alpha-dichlorotoluene; benzotrichloride; 2-chlorotoluene; 3-chlorotoluene; 4-chlorotoluene; 2-chlorobenzyl chloride; 2-chlorobenzyl fluoride; 3-chlorobenzyl chloride; 4-chlorobenzyl chloride; 4-fluorobenzyl chloride; 4-chlorobenzyl fluoride; and the like.

Particularly problematic chlorine containing hydrocarbon compounds are one or more compounds selected from the group consisting of: trichlorofluoromethane, hexafluorochloropropane, chlorotetrafluoropropene, chlorotrifluoropropene, 1,1-dichloro-2,2-difluoroethene, and pentafluoro-2-chloropropene.

In one embodiment, the polymerization process is carried out to form a polymer in a mixture that comprises a catalyst system, at least one monomer and hydrofluorocarbon, such that no single chlorine containing hydrocarbon compound is at a concentration of greater than 40 ppma. Preferably, no single chlorine containing hydrocarbon compound is at a concentration of greater than 30 ppma, more preferably greater than 25 ppma, and most preferably greater than 20 ppma. The used of the term "no single chlorine containing compound" means that no single one of any chlorine containing hydrocarbon should be present in the diluent used according to this invention, particularly any single one of the chlorine containing hydrocarbons referenced in the formula $Cl_aF_bC_cH_d$ or specifically described herein.

In an alternative embodiment, productivity of the polymerization process of this invention is sufficiently high when the mixture in which the polymer is produced contains no single chlorine containing hydrocarbon compound at a volume concentration greater than 40 ppmv. Preferably, the mixture in which the polymer is produced contains no single chlorine containing hydrocarbon compound at a volume concentration greater than 20 ppmv, more preferably no greater than 10 ppmv, still more preferably no greater than 5 ppmv, and most preferably no greater than 2 ppmv.

In another embodiment of the invention, the diluent contains a total amount of chlorine containing hydrocarbons of not greater than 200 ppma. Preferably, the diluent contains a total amount of chlorine containing hydrocarbons of not greater than 150 ppma, more preferably not greater than 100 ppma, and most preferably not greater than 50 ppma.

IV. Removal of Chlorine Containing Hydrocarbons

The chlorine containing hydrocarbon compounds are typically found in HFC compositions as a result of HFC manufacturing processes. The HFC manufacturing process are generally carried out by replacing chlorine atoms of a chlorine containing hydrocarbon with one or more fluorine atoms. Such processes can be carried out, for example, using HF or alkali metal fluoride reaction processes. The result is that chlorine containing by-products can be left in the HFC material.

According to this invention, it is preferred that all, or substantially all, of the chlorine containing compounds be removed from the HFC compositions that are to be used as a diluent in polymerization reaction processes. Any process capable of removing the chlorine containing compound or compounds to the desired or predetermined level can be used.

The HFC compositions that can be treated according to this invention can comprise a significant amount of chlorine containing hydrocarbon compounds. In one embodiment, the HFC composition to be treated comprises a total amount of chlorine containing hydrocarbons of 50,000 ppm or less, by mass. Preferably, HFC compositions to be treated are pretreated as by distillation and submitted to further processing to lower the amount of chlorine containing hydrocarbons. Such HFC compositions preferably contain a total amount of chlorine containing hydrocarbons of not greater than 5,000 ppm, more preferably not greater than 1,000 ppm, and most preferably not greater than 500 ppm, by mass. Generally the HFC composition to be treated is distilled, and the distilled portion is further treated. In a preferred embodiment, the HFC composition is distilled and the distilled fraction comprises a total amount of chlorine containing hydrocarbons of from 1 to 50,000 ppm by mass, or from 5 to 25,000 ppm by mass, or from 10 to 10,000 ppm by mass.

In one embodiment, the chlorine containing hydrocarbon compound or compounds are separated using extractive or azeotropic distillation. In this embodiment, the hydrofluorocarbon mixture containing the chlorine containing hydrocarbon compound is distilled using a volatility increasing extractant. For example, butane can be used as such an extractant. Such an embodiment is more completely described in U.S. Pat. No. 3,819,493, which is incorporated herein by reference.

In another embodiment, the chlorine containing hydrocarbon compound or compounds are separated using metal permanganate. Preferably the hydrofluorocarbon mixture containing the chlorine containing hydrocarbon compound is contacted with a metal permanganate in a liquid medium. Aqueous or non-aqueous solvents can be used in the process. The permanganate is preferably an alkali metal or alkaline earth metal permanganate, and the permanganate solution can be in acid, neutral or alkaline solution. Sodium and potassium permanganates are preferred. More preferably, potassium permanganate is used in the aqueous phase. Aqueous permanganate treatment is preferably carried out at a temperature of from 10° C. to the boiling point of the mixture, for example from 10° C. to 40° C. The time of treatment with aqueous permanganate can vary as desired. Treatment times in the range of from 5 minutes to 90 minutes are preferred. Such methods are more completely described in U.S. Pat. No. 4,129,603, which is incorporated herein by reference.

Removal of the chlorine containing hydrocarbon compound or compounds can also be carried out using chromium oxide or basic chromium fluoride. The hydrofluorocarbon mixture containing the chlorine containing hydrocarbon compound is preferably passed into a reactor containing the chromium oxide or chromium fluoride. The reactor is generally operated at a temperature of from 100° C. to 275° C., preferably from 125° C. to 250° C. Contact times are generally in the range of from 2 to 20 seconds, preferably from 3 to 15 seconds. Atmospheric or superatmospheric pressures can be used. Such methods are greater detailed, for example, in U.S. Pat. No. 4,158,675, the descriptions of which are incorporated herein by reference.

In various preferred embodiments, the chlorine containing hydrocarbons can be reduced or removed using one or more adsorbents. Non-limiting examples of suitable adsorbents include activated carbon, and molecular sieves. Preferred molecular sieves include zeolites, metalloaluminates and aluminophosphates. The molecular sieves useful in the invention have an average pore size of from about 3 to 15 angstroms.

In one embodiment, the adsorbent is activated carbon having a particle size from about 4 to 325 mesh. Preferably the particle size of the activated carbon is from 6 to 100 mesh, more preferably from 10 to 30 mesh.

In one embodiment, the adsorbent is a molecular sieve having an average pore opening of from about 7 angstroms to 10 angstroms. Alternatively, the average pore opening ranges from greater than 7 angstroms to 9 angstroms or from greater than 7 angstroms to 8 angstroms.

In another embodiment, the adsorbent is a molecular sieve having an average pore size of 3 angstroms to 6 angstroms. In particular, the adsorbent can be a 3A, 4A or 5A molecular sieve, particularly zeolite type molecular sieves.

Other examples of zeolites that can be used as adsorbents include zeolite-beta and zeolite-Y. Any of the zeolites used as an adsorbent according to this invention can be ion exchanged. Examples of such ions include hydrogen, potassium, sodium and calcium.

The adsorbent is preferably in particulate form, and more particularly in the form of pellets. Preferably, the adsorbent has a surface area of from 300 to 900 m²/g.

The adsorbent is also preferably pre-treated prior to use by heating in a dry gas stream, such as with dry air or nitrogen. Typical temperatures for the pre-treatment are from 100° C. to 400° C.

Adsorption of the chlorine containing hydrocarbons can be carried out in any type of system capable of producing the desired hydrofluorocarbon product. For example, the absorption process can be carried out in one or more stationary packed beds, counter current moving beds, fluidized beds or any combination thereof.

Adsorption can be carried out in the liquid phase or the gas phase. In a preferred embodiment, the hydrofluorocarbon containing the chlorine containing hydrocarbon is pre-treated, for example, by distillation or extractive distillation, and then contacted with the adsorbent.

Suitable temperatures suitable for adsorption techniques range from about −20° C. to 300° C. Suitable pressures range from about 10 kPa to 3,000 kPa.

Following adsorption, the adsorbent is preferably regenerated and reused. Such process is generally referred as desorption, since the adsorbed compound or compounds are desorbed from the adsorbent. Desorption of the compounds held by the adsorbent can be achieved by maintaining the adsorbent in place, or removing the adsorbent and desorbing the compounds at a remote location. In a preferred embodiment, the adsorbent is left in place. Preferably a purge material is used to desorb the adsorbed material. Examples of purge materials include nitrogen and air.

In another embodiment, the chlorine containing hydrocarbons are reduced or removed using reactive distillation. In general, reactive distillation involves hydrofluorination or halogen (e.g., chlorine) substitution while simultaneously distilling off hydrofluorocarbon product. Reactive distillation can be performed with or without a catalyst, although the use if a catalyst is preferred. Examples of suitable catalysts include, but are not limited to, $BF_3$, $SnCl_4$, a bifluoride catalyst, chromium oxide, and the like. Examples of a bifluoride catalyst include sodium fluoride, cesium fluoride, and ammonium fluoride. Alternatively, the catalyst can be made in situ by reacting a Lewis base with HF, for example, the reaction of amines with HF. Greater details of reaction distillation processes are disclosed in WO 96/40406, the descriptions of which are incorporated herein by reference.

In yet another embodiment, the chlorine containing hydrocarbons are reduced or removed using one or more decomposing agents. An example of a decomposing agent is iron oxide. Preferably the decomposing agent comprises iron oxide and an alkaline earth metal. In a preferred embodiment, the is a ferric oxide, more preferably a gamma-iron hydroxide oxide and/or a gamma-ferric oxide. Preferred as an alkaline earth metal is at least one compound selected from the group consisting of oxides, hydroxides and carbonates of an alkaline earth metal of magnesium, calcium, strontium or barium.

In one embodiment, the decomposing agent contains from 5% to 40% by mass of an iron oxide and from 60% to 95% by mass of an alkaline earth metal compound, based on the entire mass of the impurity decomposing agent. The decomposing agent preferably is in granular form, and more preferably comprises iron oxide powder has an average particle size of 100 microns or less and alkaline earth metal powder having an average particles of 100 microns or less. More preferably, the granule has an average particle size of 0.5 to 10 mm. Decomposition is preferably carried out by contacting the hydrofluorocarbon containing the chlorine containing hydrocarbons with the decomposing agent at a temperature of 250° C. to 380° C. Additional details of decomposition agents and processes are set forth in WO 02/055457, which details are incorporated herein by reference.

V. Catalyst System

A. Catalyst Compounds

The catalyst system used in the polymerization process will typically comprise a catalyst compound, and an activator compound, and may also include support materials and one or more co-catalysts. The components of the catalyst system are chosen to be capable of being utilized in the polymerization process selected. For example, polymerization may be conducted in a slurry and/or in a solution where the slurry and solution are used separately or combined and introduced into a polymerization reactor. The catalyst compounds which may be utilized in the catalyst systems of the invention for such polymerizations include: bulky ligand metallocene compounds; transition metal catalysts (e.g., Ziegler Natta, Phillips); Group 15 containing metal compounds; phenoxide catalyst compounds; and additionally discovered catalyst compounds. The catalysts, co-catalysts and activator compounds can include the support materials. As used herein, the new notation numbering scheme for the Periodic Table Groups are used as set out in Chemical And Engineering News, 63(5), 27 (1985).

In some embodiments, however, it is preferred that the catalyst system not comprise titanium tetrachloride, particularly not the combination of $TiCl_4$ and aluminum alkyl (such as triethylaluminum), particularly when the FC is a perfluorocarbon. In situations where the catalyst is titanium tetrachloride, particularly the combination of $TiCl_4$ and aluminum alkyl (such as triethylaluminum) the FC is preferably a hydrofluorocarbon. In another embodiment, the catalyst is not a free radical initiator, such as a peroxide.

1. Bulky Ligand Metallocenes

The catalyst compositions used in carrying out the invention may include one or more bulky ligand metallocene compounds (also referred to herein as metallocenes). Typical bulky ligand metallocene compounds are generally described as containing one or more bulky ligand(s) and one or more leaving group(s) bonded to at least one metal atom. The bulky ligands are generally represented by one or more open, acyclic, or fused ring(s) or ring system(s) or a combination thereof. These bulky ligands, preferably the ring(s) or ring system(s) are typically composed of atoms selected from Groups 13 to 16 atoms of the Periodic Table of Elements; preferably the atoms are selected from the group consisting of carbon, nitrogen, oxygen, silicon, sulfur, phosphorous, germanium, boron and aluminum or a combination thereof. Most preferably, the ring(s) or ring system(s) are composed of carbon atoms such as but not limited to those cyclopentadienyl ligands or cyclopentadienyl-type ligand structures or other similar functioning ligand structure such as a pentadiene, a cyclooctatetraendiyl or an imide ligand. The metal atom is preferably selected from Groups 3 through 15 and the lanthanide or actinide series of the Periodic Table of Elements. Preferably the metal is a transition metal from Groups 4 through 12, more preferably Groups 4, 5 and 6, and most preferably the transition metal is from Group 4.

In one embodiment, the catalyst composition includes one or more bulky ligand metallocene catalyst compounds represented by the formula:

$$L^A L^B MQ_n \qquad (I)$$

where M is a metal atom from the Periodic Table of the Elements and may be a Group 3 to 12 metal or from the lanthanide or actinide series of the Periodic Table of Elements, preferably M is a Group 4, 5 or 6 transition metal, more preferably M is a Group 4 transition metal, even more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, borabenzene ligands and the like, including hydrogenated versions thereof, for example tetrahydroindenyl ligands. In one embodiment, $L^A$ and $L^B$ may be any other ligand structure capable of π-bonding to M. In yet another embodiment, the atomic molecular weight (MW) of $L^A$ or $L^B$ exceeds 60 a.m.u., preferably greater than 65 a.m.u. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of Formula III only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris (trifluoromethyl)-silyl, methyl-bis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. In one embodiment, Q is a monoanionic labile ligand having a sigma-bond to M. Depending on the oxidation state of the metal, the value for n is 0, 1 or 2 such that Formula III above represents a neutral bulky ligand metallocene catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like.

In another embodiment, the catalyst composition may include one or more bulky ligand metallocene catalyst compounds where $L^A$ and $L^B$ of Formula I are bridged to each other by at least one bridging group, A, as represented by Formula II.

$$L^A A L^B M Q_n \tag{II}$$

The compounds of Formula II are known as bridged, bulky ligand metallocene catalyst compounds. $L^A$, $L^B$, M, Q and n are as defined above. Non-limiting examples of bridging group A include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group A may also contain substituent groups R as defined above including halogens and iron. Non-limiting examples of bridging group A may be represented by R'$_2$C, R'$_2$Si, R'$_2$Si R'$_2$Si, R'$_2$Ge, R'P, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of Formula II have two or more bridging groups A (EP 664 301 B1).

In another embodiment, the bulky ligand metallocene catalyst compounds are those where the R substituents on the bulky ligands $L^A$ and $L^B$ of Formulas I and II are substituted with the same or different number of substituents on each of the bulky ligands. In another embodiment, the bulky ligands $L^A$ and $L^B$ of Formulas I and II are different from each other.

Other bulky ligand metallocene catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are herein fully incorporated by reference.

In another embodiment, the catalyst compositions may include bridged heteroatom, mono-bulky ligand metallocene compounds. These types of catalysts and catalyst systems are described in, for example, PCT publication WO 92/00333, WO 94/07928, WO 91/04257, WO 94/03506, WO96/00244, WO 97/15602 and WO 99/20637 and U.S. Pat. Nos. 5,057, 475, 5,096,867, 5,055,438, 5,198,401, 5,227,440 and 5,264, 405 and European publication EP-A-0 420 436, all of which are herein fully incorporated by reference.

In another embodiment, the catalyst composition includes one or more bulky ligand metallocene catalyst compounds represented by Formula III:

$$L^CAJMQ_n \qquad\qquad (III)$$

where M is a Group 3 to 16 metal atom or a metal selected from the Group of actinides and lanthanides of the Periodic Table of Elements, preferably M is a Group 4 to 12 transition metal, and more preferably M is a Group 4, 5 or 6 transition metal, and most preferably M is a Group 4 transition metal in any oxidation state, especially titanium; $L^C$ is a substituted or unsubstituted bulky ligand bonded to M; J is bonded to M; A is bonded to J and $L^C$; J is a heteroatom ancillary ligand; and A is a bridging group; Q is a univalent anionic ligand; and n is the integer 0, 1 or 2. In Formula III above, $L^C$, A and J form a fused ring system. In an embodiment, $L^C$ of Formula III is as defined above for $L^A$. A, M and Q of Formula III are as defined above in Formula I.

In Formula III J is a heteroatom containing ligand in which J is an element with a coordination number of three from Group 15 or an element with a coordination number of two from Group 16 of the Periodic Table of Elements. Preferably J contains a nitrogen, phosphorus, oxygen or sulfur atom with nitrogen being most preferred. In a preferred embodiment, when the catalyst system comprises compounds represented by Formula III, the fluorocarbon preferably is a hydrofluorocarbon. Preferably, when the catalyst system comprises compounds represented by Formula III, the fluorocarbon is not a perfluorocarbon.

In an embodiment of the invention, the bulky ligand metallocene catalyst compounds are heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene catalyst compounds are described in WO 96/33202, WO 96/34021, WO 97/17379 and WO 98/22486 and EP-A1-0 874 005 and U.S. Pat. Nos. 5,637,660, 5,539,124, 5,554,775, 5,756,611, 5,233,049, 5,744,417, and 5,856,258 all of which are herein incorporated by reference.

In one embodiment, the bulky ligand metallocene catalyst compounds are those complexes known as transition metal catalysts based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the bulky ligand metallocene catalyst compound is a complex of a metal, preferably a transition metal, a bulky ligand, preferably a substituted or unsubstituted pi-bonded ligand, and one or more heteroalkyl moieties, such as those described in U.S. Pat. Nos. 5,527,752 and 5,747,406 and EP-B1-0 735 057, all of which are herein fully incorporated by reference.

In another embodiment, the catalyst composition includes one or more bulky ligand metallocene catalyst compounds is represented by Formula IV:

$$L^DMQ_2(YZ)X_n \qquad\qquad (IV)$$

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and $Q_2(YZ)$ forms a ligand, preferably a unicharged polydentate ligand; or Q is a univalent anionic ligand also bonded to M; X is a univalent anionic group when n is 2 or X is a divalent anionic group when n is 1; n is 1 or 2.

In Formula IV, L and M are as defined above for Formula I. Q is as defined above for Formula I, preferably Q is selected from the group consisting of —O—, —NR—, —CR2— and —S—; Y is either C or S; Z is selected from the group consisting of —OR, —NR2, —CR3, —SR, —SiR3, —PR2, —H, and substituted or unsubstituted aryl groups, with the proviso that when Q is —NR— then Z is selected from one of the group consisting of —OR, —NR2, —SR, —SiR3, —PR2 and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

In another embodiment, the bulky ligand metallocene catalyst compounds are those described in PCT publications WO 99/01481 and WO 98/42664, which are fully incorporated herein by reference.

Useful Group 6 bulky ligand metallocene catalyst systems are described in U.S. Pat. No. 5,942,462, which is incorporated herein by reference.

Still other useful catalysts include those multinuclear metallocene catalysts as described in WO 99/20665 and U.S. Pat. No. 6,010,794, and transition metal metaaracyle structures described in EP 0 969 101 A2, which are herein incorporated herein by reference. Other metallocene catalysts include those described in EP 0 950 667 A1, double cross-linked metallocene catalysts (EP 0 970 074 A1), tethered metallocenes (EP 970 963 A2) and those sulfonyl catalysts described in U.S. Pat. No. 6,008,394, which are incorporated herein by reference.

It is also contemplated that in one embodiment the bulky ligand metallocene catalysts, described above, include their structural or optical or enantiomeric isomers (meso and racemic isomers, for example see U.S. Pat. No. 5,852,143, incorporated herein by reference) and mixtures thereof.

2. Transition Metal Compounds

In another embodiment, conventional-type transition metal catalysts may be used in the practice of this invention. Conventional-type transition metal catalysts are those traditional Ziegler-Natta, vanadium and Phillips-type catalysts well known in the art. Such as, for example Ziegler-Natta catalysts as described in *Ziegler-Natta Catalysts and Polymerizations*, John Boor, Academic Press, New York, 1979. Examples of conventional-type transition metal catalysts are also discussed in U.S. Pat. Nos. 4,115,639, 4,077,904, 4,482,687, 4,564,605, 4,721,763, 4,879,359 and 4,960,741, all of which are herein fully incorporated by reference. The conventional-type transition metal catalyst compounds that may be used in the present invention include transition metal compounds from Groups 3 to 17, preferably 4 to 12, more preferably 4 to 6 of the Periodic Table of Elements.

Preferred conventional-type transition metal catalysts may be represented by the formula: $MR_x$, where M is a metal from Groups 3 to 17, preferably Group 4 to 6, more preferably Group 4, most preferably titanium; R is a halogen or a hydrocarboyloxy group; and x is the oxidation state of the metal M. Non-limiting examples of R include alkoxy, phenoxy, bromide, chloride and fluoride. Non-limiting examples of conventional-type transition metal catalysts where M is titanium include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3.⅓AlCl_3$ and $Ti(OC_{12}H_{25})Cl_3$.

Conventional-type transition metal catalyst compounds based on magnesium/titanium electron-donor complexes that are useful in the invention are described in, for example, U.S. Pat. Nos. 4,302,565 and 4,302,566, which are herein fully incorporate by reference. The $MgTiCl_6$ (ethyl acetate)$_4$ derivative is particularly preferred.

British Patent Application 2,105,355 and U.S. Pat. No. 5,317,036, herein incorporated by reference, describes various conventional-type vanadium catalyst compounds. Non-limiting examples of conventional-type vanadium catalyst compounds include vanadyl trihalide, alkoxy halides and alkoxides such as $VOCl_3$, $VOCl_2(OBu)$ where Bu=butyl and $VO(OC_2H_5)_3$; vanadium tetra-halide and vanadium alkoxy halides such as $VCl_4$ and $VCl_3(OBu)$; vanadium and vanadyl acetyl acetonates and chloroacetyl acetonates such as $V(AcAc)_3$ and $VOCl_2(AcAc)$ where (AcAc) is an acetyl acetonate. The preferred conventional-type vanadium catalyst compounds are $VOCl_3$, $VCl_4$ and $VOCl_2$—OR where R is a hydrocarbon radical, preferably a $C_1$ to $C_{10}$ aliphatic or aromatic hydrocarbon radical such as ethyl, phenyl, isopropyl, butyl, propyl, n-butyl, iso-butyl, tertiary-butyl, hexyl, cyclohexyl, naphthyl, etc., and vanadium acetyl acetonates.

Conventional-type chromium catalyst compounds, often referred to as Phillips-type catalysts, suitable for use in the present invention include $CrO_3$, chromocene, silyl chromate, chromyl chloride ($CrO_2Cl_2$), chromium-2-ethyl-hexanoate, chromium acetylacetonate ($Cr(AcAc)_3$), and the like. Non-limiting examples are disclosed in U.S. Pat. Nos. 3,709,853, 3,709,954, 3,231,550, 3,242,099 and 4,077,904, which are herein fully incorporated by reference.

Still other conventional-type transition metal catalyst compounds and catalyst systems suitable for use in the present invention are disclosed in U.S. Pat. Nos. 4,124,532, 4,302,565, 4,302,566, 4,376,062, 4,379,758, 5,066,737, 5,763,723, 5,849,655, 5,852,144, 5,854,164 and 5,869,585 and published EP-A2 0 416 815 A2 and EP-A1 0 420 436, which are all herein incorporated by reference.

Other catalysts may include cationic catalysts such as $AlCl_3$, and other cobalt, iron, nickel and palladium catalysts well known in the art. See for example U.S. Pat. Nos. 3,487,112, 4,472,559, 4,182,814 and 4,689,437, all of which are incorporated herein by reference.

It is also contemplated that other catalysts can be combined with the catalyst compounds in the catalyst composition of the invention. For example, see U.S. Pat. Nos. 4,937,299, 4,935,474, 5,281,679, 5,359,015, 5,470,811, and 5,719,241 all of which are herein fully incorporated herein reference.

It is further contemplated that one or more of the catalyst compounds described above or catalyst systems may be used in combination with one or more conventional catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010 published Aug. 1, 1996, all of which are herein fully incorporated by reference.

3. Group 15 Catalysts

In one embodiment, the catalyst compounds utilized in the invention include one or more Group 15 containing metal catalyst compounds. The Group 15 containing compound generally includes a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group.

In one embodiment, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In another embodiment, the Group 15 containing metal compound may be represented by the formulae:

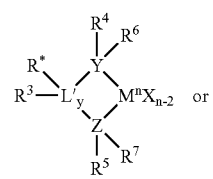

Formula V

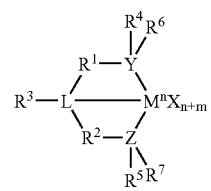

Formula VI wherein:

M is a Group 3 to 12 transition metal or a Group 13 or 14 main group metal, preferably a Group 4, 5, or 6 metal, and more preferably a Group 4 metal, and most preferably zirconium, titanium or hafnium;

X is independently a leaving group, preferably, an anionic leaving group, and more preferably hydrogen, a hydrocarbyl group, a heteroatom or a halogen, and most preferably an alkyl;

y is 0 or 1 (when y is 0 group L' is absent);

n is the oxidation state of M, preferably +3, +4, or +5, and more preferably +4;

m is the formal charge of the YZL or the YZL' ligand, preferably 0, −1, −2 or −3, and more preferably −2;

L is a Group 15 or 16 element, preferably nitrogen;
L' is a Group 15 or 16 element or Group 14 containing group, preferably carbon, silicon or germanium;
Y is a Group 15 element, preferably nitrogen or phosphorus, and more preferably nitrogen;
Z is a Group 15 element, preferably nitrogen or phosphorus, and more preferably nitrogen;
$R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group, wherein $R^1$ and $R^2$ may also be interconnected to each other;
$R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen;
$R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group;
$R^1$ and $R^2$ may be interconnected to each other, and/or $R^4$ and $R^5$ may be interconnected to each other;
$R^6$ and $R^7$ are independently absent, hydrogen, an alkyl group, halogen, heteroatom, or a hydrocarbyl group, preferably a linear, cyclic or branched alkyl group having 1 to 20 carbon atoms, and more preferably absent; and
$R^*$ is absent, or is hydrogen, a Group 14 atom containing group, a halogen, or a heteroatom containing group.

By "formal charge of the YZL or YZL' ligand", it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In a preferred embodiment R4 and R5 are independently a group represented by the following formula:

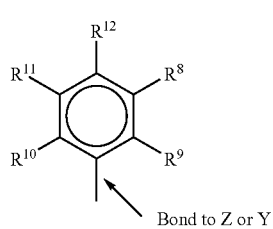

Formula 1 wherein:
$R^8$ to $R^{12}$ are each independently hydrogen, a $C_1$ to $C_{40}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group, wherein the cyclic groups may be aromatic.

In a preferred embodiment of Formula 1, R9, R10 and R12 are independently a methyl, ethyl, propyl or butyl group (including all isomers). In another preferred embodiment, R9, R10 and R12 are methyl groups, and R8 and R11 are hydrogen.

In a particularly preferred embodiment R4 and R5 are both a group represented by the following formula:

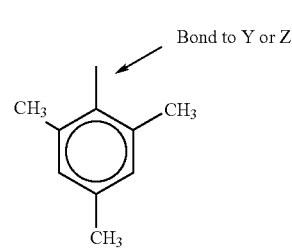

Formula 2

In this embodiment, M is a Group 4 metal, preferably zirconium, titanium or hafnium, and even more preferably zirconium; each of L, Y, and Z is nitrogen; each of R1 and R2 is —CH2—CH2—; R3 is hydrogen; and R6 and R7 are absent.

In another particularly preferred embodiment, the Group 15 containing metal compound is represented by Compound 1 below:

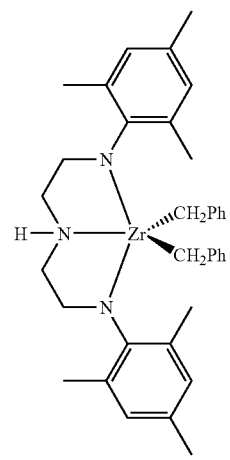

Compound 1 wherein Ph in Compound 1 equals phenyl.

The Group 15 containing metal compounds can be prepared by any appropriate method, including methods known in the art, such as those disclosed in EP 0 893 454 A1, U.S. Pat. No. 5,889,128 and the references cited in U.S. Pat. No. 5,889,128 which are all herein incorporated by reference. U.S. application Ser. No. 09/312,878, filed May 17, 1999, discloses a gas or slurry phase polymerization process using a supported bisamide catalyst, which is also incorporated herein by reference.

A preferred direct synthesis of these compounds comprises reacting the neutral ligand, (see for example YZL or YZL' of Formula V or VI) with $M''X_n$ (M is a Group 3 to 14 metal, n is the oxidation state of M, each X is an anionic group, such as halide, in a non-coordinating or weakly coordinating solvent, such as ether, toluene, xylene, benzene, methylene chloride, and/or hexane or other solvent having a boiling point above 60° C., at about 20 to about 150° C. (preferably 20 to 100° C.), preferably for 24 hours or more, then treating the mixture with an excess (such as four or more equivalents) of an alkylating agent, such as methyl magnesium bromide in ether. The magnesium salts are removed by filtration, and the metal complex isolated by standard techniques.

In one embodiment, the Group 15 containing metal compound is prepared by a method comprising reacting a neutral ligand, (see for example YZL or YZL' of Formula V or VI) with a compound represented by the formula $M''X_n$ (where M is a Group 3 to 14 metal, n is the oxidation state of M, each X is an anionic leaving group) in a non-coordinating or weakly coordinating solvent, at about 20° C. or above, preferably at about 20 to about 100° C., then treating the mixture with an excess of an alkylating agent, then recovering the metal complex. In a preferred embodiment the solvent has a boiling point above 60° C., such as toluene, xylene, benzene, and/or hexane. In another embodiment the solvent comprises ether and/or methylene chloride, either being preferable.

For additional information of Group 15 containing metal compounds, please see Mitsui Chemicals, Inc. in EP 0 893 454 A1 which discloses transition metal amides combined with activators to polymerize olefins.

In one embodiment, the Group 15 containing metal compound is allowed to age prior to use as a polymerization. It has been noted on at least one occasion that one such catalyst compound (aged at least 48 hours) performed better than a newly prepared catalyst compound.

4. Phenoxides

The catalyst composition of the invention may include one or more phenoxide catalyst compounds represented by the following formulae:

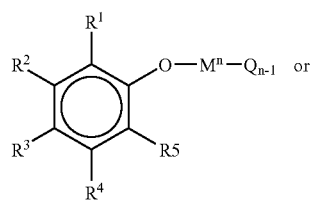

Formula (VII)

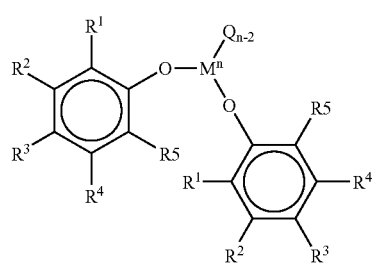

Formula (VIII)

wherein:

$R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not be bound to M;

at least one of $R^2$ to $R^5$ is a group containing a heteroatom, the rest of $R^2$ to $R^5$ are independently hydrogen or a $C_1$ to $C_{100}$ group, preferably a $C_4$ to $C_{20}$ alkyl group (preferably butyl, isobutyl, pentyl hexyl, heptyl, isohexyl, octyl, isooctyl, decyl, nonyl, dodecyl) and any of $R^2$ to $R^5$ also may or may not be bound to M;

O is oxygen;

M is a group 3 to group 10 transition metal or lanthanide metal, preferably a group 4 metal, preferably Ti, Zr or Hf; and n is the valence state of the metal M, preferably 2, 3, 4, or 5, Q is an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon silica or another heteroatom. Preferred heteroatoms include boron, aluminum, silicon, nitrogen, phosphorus, arsenic, tin, lead, antimony, oxygen, selenium, tellurium. Particularly preferred heteroatoms include nitrogen, oxygen, phosphorus, and sulfur. Even more particularly preferred heteroatoms include oxygen and nitrogen. The heteroatom itself may be directly bound to the phenoxide ring or it may be bound to another atom or atoms that are bound to the phenoxide ring. The heteroatom containing group may contain one or more of the same or different heteroatoms. Preferred heteroatom groups include imines, amines, oxides, phosphines, ethers, ketenes, oxoazolines heterocyclics, oxazolines, thioethers, and the like. Particularly preferred heteroatom groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment, Q is a bond to any of R2 to R5, and the R group that Q is bound to is a heteroatom containing group.

This invention may also be practiced with the catalysts disclosed in EP 0 874 005 A1, which in incorporated by reference herein.

5. Additional Compounds

The catalyst compositions used to carry out the invention may include one or more complexes known as transition metal catalysts based on bidentate ligands containing pyridine or quinoline moieties, such as those described in U.S. Pat. No. 6,103,657, which is herein incorporated by reference.

In one embodiment, these catalyst compounds are represented by the formula:

$$((Z)XA_t(YJ))_qMQ_n \qquad (IX)$$

where M is a metal selected from Group 3 to 13 or lanthanide and actinide series of the Periodic Table of Elements; Q is bonded to M and each Q is a monovalent, bivalent, or trivalent anion; X and Y are bonded to M; one or more of X and Y are heteroatoms, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms; t is 0 or 1; when t is 1, A is a bridging group joined to at least one of X, Y or J, preferably X and J; q is 1 or 2; n is an integer from 1 to 4 depending on the oxidation state of M. In one embodiment, where X is oxygen or sulfur then Z is optional. In another embodiment, where X is nitrogen or phosphorous then Z is present. In an embodiment, Z is preferably an aryl group, more preferably a substituted aryl group.

In one embodiment, the catalyst compounds used in this invention include complexes of Ni$^{2+}$ and Pd$^{2+}$ described in the articles Johnson, et al., "New Pd(II)- and Ni(II)-Based Catalysts for Polymerization of Ethylene and a-Olefins", *J. Am. Chem. Soc.* 1995, 117, 6414-6415 and Johnson, et al., "Copolymerization of Ethylene and Propylene with Functionalized Vinyl Monomers by Palladium(II) Catalysts", *J. Am. Chem. Soc.*, 1996, 118, 267-268, and WO 96/23010 published Aug. 1, 1996, WO 99/02472, U.S. Pat. Nos. 5,852,145, 5,866,663 and 5,880,241, which are all herein fully incorporated by reference. These complexes can be either dialkyl ether adducts, or alkylated reaction products of the described dihalide complexes that can be activated to a cationic state by the activators of this invention described below.

Other catalyst compounds include nickel complexes, such as those described in WO 99/50313, which is incorporated herein by reference.

Also included are those diimine based ligands of Group 8 to 10 metal catalyst compounds disclosed in PCT publications WO 96/23010 and WO 97/48735 and Gibson, et al., *Chem. Comm.*, pp. 849-850 (1998), all of which are herein incorporated by reference.

Other useful catalyst compounds are those Group 5 and 6 metal imido complexes described in EP-A2-0 816 384 and U.S. Pat. No. 5,851,945, which is incorporated herein by reference. In addition, metallocene catalysts include bridged bis(arylamido) Group 4 compounds described by D. H. McConville, et al., in *Organometallics* 1195, 14, 5478-5480, which is herein incorporated by reference. In addition, bridged bis(amido) catalyst compounds are described in WO 96/27439, which is herein incorporated by reference. Other useful catalysts are described as bis(hydroxy aromatic nitrogen ligands) in U.S. Pat. No. 5,852,146, which is incorporated herein by reference. Other useful catalysts containing one or more Group 15 atoms include those described in WO 98/46651, which is herein incorporated herein by reference.

B. Supports, Carriers and Techniques

In one embodiment, the catalyst composition includes a support material or carrier, and preferably includes a supported activator. For example, the catalyst composition component, preferably the activator compound and/or the catalyst compound, is deposited on, contacted with, vaporized with, bonded to, or incorporated within, adsorbed or absorbed in, or on, a support or carrier.

The support material is appropriate material, including any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

A group of preferred support materials are inorganic oxides that include Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 m2/g, pore volume in the range of from about 0.1 to about 4.0 cc/g and average particle size in the range of from about 5 to about 500 µm. More preferably, the surface area of the support material is in the range of from about 50 to about 500 m2/g, pore volume of from about 0.5 to about 3.5 cc/g and average particle size of from about 10 to about 200 µm. Most preferably the surface area of the support material is in the range is from about 100 to about 400 m2/g, pore volume from about 0.8 to about 3.0 cc/g and average particle size is from about 5 to about 100 µm. The average pore size of the carrier of the invention typically has pore size in the range of from 10 to 1000 Å, preferably 50 to about 500 Å, and most preferably 75 to about 350 Å.

The support materials may be treated chemically, for example with a fluoride compound as described in WO 00/12565, which is herein incorporated by reference. Other supported activators are described in for example WO 00/13792 that refers to supported boron containing solid acid complex.

In a preferred embodiment, fumed silica available under the trade name Cabosil™ TS-610, available from Cabot Corporation is utilized as a nucleating agent or as a viscosity builder in the catalyst component slurry discussed below. Fumed silica is typically a silica with particles 7 to 30 nanometers in size that has been treated with dimethylsilyldichloride such that a majority of the surface hydroxyl groups are capped. In another embodiment the fumed silica utilized has a particle size of less than 40 microns, preferably less than 20 microns or preferably less than 10 microns.

In a preferred method of forming a supported catalyst composition component, the amount of liquid in which the activator is present is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67-96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332-334 (March, 1956).

C. Activators and Activation Methods

The polymerization catalyst compounds useful in this invention can be activated in various ways to yield compounds having a vacant coordination site that will coordinate, insert, and polymerize olefin(s). For the purposes of this invention, the term "activator" is defined to be any compound which can activate any one of the catalyst compounds described herein by converting the neutral catalyst compound to a catalytically active catalyst cation compound. Non-limiting activators, for example, include alumoxanes, aluminum alkyls, ionizing activators, which may be neutral or ionic, and conventional-type cocatalysts.

1. Alumoxanes

In one embodiment, alumoxanes activators are utilized as a catalyst activator. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. Another alumoxane is a modified methyl alumoxane (MMAO) cocatalyst type 3A (commercially available from Akzo Chemicals, Inc. under the trade name Modified Methylaluminoxane type 3A, covered under patent number U.S. Pat. No. 5,041,584).

Aluminum Alkyl or organoaluminum compounds which may be utilized as activators include trimethylaluminum, triethylaluminum, triisobutylaluminum, tri-n-hexylaluminum, tri-n-octylaluminum and the like.

2. Ionizing Activators

It is within the scope of this invention to use an ionizing or stoichiometric activator, neutral or ionic, such as tri(n-butyl) ammonium tetrakis (pentafluorophenyl)boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

"Substituted alkyl" refers to an alkyl as described in which one or more hydrogen atoms of the alkyl is replaced by another group such as a halogen, aryl, substituted aryl, cycloalkyl, substituted cycloalkyl, and combinations thereof. Examples of substituted alkyls include, for example, benzyl, trifluoromethyl and the like.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

In a preferred embodiment, the stoichiometric activators include a cation and an anion component, and may be represented by the following formula:

$$(L-H)_d^+ \cdot (A^{d-}) \qquad (X)$$

wherein:
L is an neutral Lewis base;
H is hydrogen;
$(L-H)^+$ is a Bronsted acid
$A^{d-}$ is a non-coordinating anion having the charge d−
d is an integer from 1 to 3.

The cation component, $(L-H)_d^+$ may include Bronsted acids such as protons or protonated Lewis bases or reducible Catalysts capable of protonating or abstracting a moiety, such as an alkyl or aryl, from the bulky ligand metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L-H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ includes those having the formula $[M^{k+}Q_n]^{d-}$ wherein k is an integer from 1 to 3; n is an integer from 2-6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Most preferably, the ionic stoichiometric activator $(L-H)^{d+} \cdot (A^{d-})$ is N,N-dimethylanilinium tetra(perfluorophenyl)borate or triphenylcarbenium tetra(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

3. Additional Activators

Other activators include those described in PCT publication WO 98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP-B1 0 573 120, PCT publications WO 94/07928 and WO 95/14044 and U.S. Pat. Nos. 5,153,157 and 5,453,410 all of which are herein fully incorporated by reference.

Other suitable activators are disclosed in WO 98/09996, incorporated herein by reference, which describes activating bulky ligand metallocene catalyst compounds with perchlorates, periodates and iodates including their hydrates. WO 98/30602 and WO 98/30603, incorporated by reference, describe the use of lithium (2,2'-bisphenyl-ditrimethylsilicate).4THF as an activator for a bulky ligand metallocene catalyst compound. WO 99/18135, incorporated herein by reference, describes the use of organo-boron-aluminum acitivators. EP-B1-0 781 299 describes using a silylium salt in combination with a non-coordinating compatible anion. Also, methods of activation such as using radiation (see EP-B B1-0 615 981 herein incorporated by reference), electrochemical oxidation, and the like are also contemplated as activating methods for the purposes of rendering the neutral bulky ligand metallocene catalyst compound or precursor to a bulky ligand metallocene cation capable of polymerizing olefins. Other activators or methods for activating a bulky ligand metallocene catalyst compound are described in for example, U.S. Pat. Nos. 5,849,852, 5,859,653 and 5,869,723 and WO 98/32775, WO 99/42467 (dioctadecylmethylammonium-bis (tris(pentafluorophenyl)borane)benzimidazolide), which are herein incorporated by reference.

Another suitable ion forming, activating cocatalyst comprises a salt of a cationic oxidizing agent and a noncoordinating, compatible anion represented by the formula: $(OX^{e+})_d$ $(A^{d-})_e$ wherein: $OX^{e+}$ is a cationic oxidizing agent having a charge of e+; e is an integer from 1 to 3; and $A^-$, and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activators, especially tetrakis(pentafluorophenyl)borate.

It within the scope of this invention that catalyst compounds can be combined with one or more activators or used in one or more activation methods described above. For example, a combination of activators has been described in U.S. Pat. Nos. 5,153,157 and 5,453,410, European publication EP-B1 0 573 120, and PCT publications WO 94/07928 and WO 95/14044. These documents all discuss the use of an alumoxane and an ionizing activator with a bulky ligand metallocene catalyst compound.

4. Supported Activators

Many supported activators are described in various patents and publications which include: U.S. Pat. No. 5,728,855 directed to the forming a supported oligomeric alkylaluminoxane formed by treating a trialkylaluminum with carbon dioxide prior to hydrolysis; U.S. Pat. No. 5,831,109 and 5,777,143 discusses a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856, 255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of a alumoxane impregnated support and a metallocene and a bulky aluminum alkyl and methylalumoxane; EP-B1-0 662 979 discusses the use of a metallocene with a catalyst support of silica reacted with alumoxane; PCT WO 96/16092 relates to a heated support treated with alumoxane and washing to remove unfixed alumoxane; U.S. Pat. Nos. 4,912,075, 4,937, 301, 5,008,228, 5,086,025, 5,147,949, 4,871,705, 5,229,478, 4,935,397, 4,937,217 and 5,057,475, and PCT WO 94/26793 all directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organoaluminuim compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker; U.S. Pat. Nos. 5,332,706, 5,473,028, 5,602,067 and 5,420,220 discusses a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relates to a process for preparing one or more alkylaluminoxanes immobilized on a solid, particulate inert support; and EP-A1-0 819 706 relates to a process for preparing a solid silica treated with alumoxane. Also, the following articles, also fully incorporated herein by reference for purposes of disclosing useful supported activators and methods for their preparation, include: W. Kaminsky, et al., "Polymerization of Styrene with Supported Half-Sandwich Complexes," *Journal of Polymer Science*, Vol. 37, 2959-2968 (1999) describes a process of adsorbing a methylalumoxane to a support followed by the adsorption of a metallocene; Junting Xu, et al. "Characterization of isotactic polypropylene prepared with dimethylsilyl bis(1-indenyl)zirconium dichloride supported on methylaluminoxane pretreated silica," *European Polymer Journal*, 35 (1999) 1289-1294, discusses the use of silica treated with methylalumoxane and a metallocene; Stephen O'Brien, et al., "EXAFS analysis of a chiral alkene polymerization catalyst incorporated in the mesoporous silicate MCM-41," *Chem. Commun.*, 1905-1906 (1997) discloses an immobilized alumoxane on a modified mesoporous silica; and F. Bonini, et al., "Propylene Polymerization through Supported Metallocene/ MAO Catalysts: Kinetic Analysis and Modeling," *Journal of Polymer Science*, Vol. 33 2393-2402 (1995) discusses using a methylalumoxane supported silica with a metallocene. Any of the methods discussed in these references are useful for producing the supported activator component utilized in the catalyst composition of the invention and all are incorporated herein by reference.

In another embodiment, the supported activator, such as supported alumoxane, is aged for a period of time prior to use herein. For reference please refer to U.S. Pat. Nos. 5,468,702 and 5,602,217, incorporated herein by reference.

In an embodiment, the supported activator is in a dried state or a solid. In another embodiment, the supported activator is in a substantially dry state or a slurry, preferably in a mineral oil slurry.

In another embodiment, two or more separately supported activators are used, or alternatively, two or more different activators on a single support are used.

In another embodiment, the support material, preferably partially or totally dehydrated support material, preferably 200° C. to 600° C. dehydrated silica, is then contacted with an organoaluminum or alumoxane compound. Preferably in an embodiment where an organoaluminum compound is used, the activator is formed in situ on and in the support material as a result of the reaction of, for example, trimethylaluminum and water.

In another embodiment, Lewis base-containing supports are reacted with a catalyst activator to form a support bonded catalyst compound. The Lewis base hydroxyl groups of silica are exemplary of metal/metalloid oxides where this method of bonding to a support occurs. This embodiment is described in U.S. Pat. No. 6,147,173, which is herein incorporated by reference.

Other embodiments of supporting an activator are described in U.S. Pat. No. 5,427,991, where supported non-coordinating anions derived from trisperfluorophenyl boron are described; U.S. Pat. No. 5,643,847 discusses the reaction of Group 13 catalyst compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions; immobilized Group IIIA Catalyst catalysts suitable for carbocationic polymerizations are described in U.S. Pat. No. 5,288,677; and James C. W. Chien, *Jour. Poly. Sci.: PtA: Poly. Chem*, Vol. 29, 1603-1607 (1991), describes the olefin polymerization utility of methylalumoxane (MAO) reacted with silica ($SiO_2$) and metallocenes and describes a covalent bonding of the aluminum atom to the silica through an oxygen atom in the surface hydroxyl groups of the silica.

In a preferred embodiment, a supported activator is formed by preparing in an agitated, and temperature and pressure controlled vessel a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40 to 120° C. and pressures from 5 psia to 20 psia (34.5 to 138 kPa). An inert gas sweep can also be used in assist in removing solvent. Alternate orders of addition, such as slurrying the support material in an appropriate solvent then adding the activator, can be used.

In another embodiment a support is combined with one or more activators and is spray dried to form a supported activator. In a preferred embodiment, fumed silica is combined with methyl alumoxane and then spray dried to from supported methyl alumoxane. Preferably a support is combined with alumoxane, spray dried and then placed in mineral oil to form a slurry useful in the instant invention.

D. Cocatalysts

Cocatalysts that can be used according to this invention include one or more cocatalysts represented by the formula:

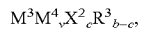

$M^3M^4_vX^2_cR^3_{b-c}$, wherein $M^3$ is a metal from Group 1 to 3 and 12 to 13 of the Periodic Table of Elements; $M^4$ is a metal of Group 1 of the Periodic Table of Elements; v is a number from 0 to 1; each $X^2$ is any halogen; c is a number from 0 to 3; each $R^3$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula $M^3R^3_k$, where $M^3$ is a Group IA, IIA, IIB or IIIA metal, such as lithium, sodium, beryllium, barium, boron, aluminum, zinc, cadmium, and gallium; k equals 1, 2 or 3 depending upon the valency of $M^3$ which valency in turn normally depends upon the particular Group to which $M^3$ belongs; and each $R^3$ may be any monovalent hydrocarbon radical.

Non-limiting examples of conventional-type organometallic cocatalyst compounds useful with the conventional-type catalyst compounds described above include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, the aluminum alkyls, such as tri-hexyl-aluminum, triethylaluminum, trimethylaluminum, and tri-isobutylaluminum. Other conventional-type cocatalyst compounds include mono-organohalides and hydrides of Group 2 metals, and mono-or di-organohalides and hydrides of Group 3 and 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, di-bromo-aluminum hydride and bromocadmium hydride. Conventional-type organometallic cocatalyst compounds are known to those in the art and a more complete discussion of these compounds may be found in U.S. Pat. Nos. 3,221,002 and 5,093,415, which are herein fully incorporated by reference.

E. Spray Dried Catalysts

In another embodiment, the catalyst compounds described are combined with support material(s) and/or activator(s) and spray dried. In another embodiment, the catalyst compounds and/or the activators are combined with a support material such as a particulate filler material and then spray dried, preferably to form a free flowing powder.

Spray drying may be by any means known in the art. Please see EP A 0 668 295 B1, U.S. Pat. Nos. 5,674,795 and 5,672,669 and U.S. patent application Ser. No. 09/464,114 filed Dec. 16, 1999, which particularly describe spray drying of supported catalysts. In general one may spray dry the catalysts by placing the catalyst compound and the optional activator in solution (allowing the catalyst compound and activator to react, if desired), adding a filler material such as silica or fumed silica, such as Gasil™ or Cabosil™, then forcing the solution at high pressures through a nozzle. The solution may be sprayed onto a surface or sprayed such that the droplets dry in midair. The method generally employed is to disperse the silica in toluene, stir in the activator solution, and then stir in the catalyst compound solution. Typical slurry concentrations are about 5 to 8 wt %. This formulation may sit as a slurry for as long as 30 minutes with mild stirring or manual shaking to keep it as a suspension before spray-drying. In one preferred embodiment, the makeup of the dried material is about 40-50 wt % activator (preferably alumoxane), 50-60 $SiO_2$ and about~2 wt % catalyst compound.

In another embodiment, fumed silica such as such as Gasil™ or Cabosil™ may be added to a solution containing a catalyst compound such that when that solution is added to the catalyst component slurry or injected into a polymerization reactor, the fumed silica acts as a template for in situ spray drying.

For simple catalyst compound mixtures, the two or more catalyst compounds can be added together in the desired ratio in the last step. In another embodiment, more complex procedures are possible, such as addition of a first catalyst compound to the activator/filler mixture for a specified reaction time t, followed by the addition of the second catalyst compound solution, mixed for another specified time x, after which the mixture is cosprayed. Lastly, another additive, such as 1-hexene in about 10 vol % can be present in the activator/filler mixture prior to the addition of the first metal catalyst compound.

In another embodiment binders are added to the mix. These can be added as a means of improving the particle morphology, i.e. narrowing the particle size distribution, lower porosity of the particles and allowing for a reduced quantity of alumoxane, which acts as the binder.

In another embodiment a solution of a bulky ligand metallocene compound and optional activator can be combined with a different slurried spray dried catalyst compound and then introduced into a reactor.

The spray dried particles are generally fed into the polymerization reactor as a mineral oil slurry. Solids concentrations in oil are about 10 to 30 weight %, preferably 15 to 25 weight %. In some embodiments, the spray dried particles can be from less than about 10 micrometers in size up to about 100 micrometers, compared to conventional supported catalysts which are about 50 micrometers. In a preferred embodiment the support has an average particle size of 1 to 50 microns, preferably 10 to 40 microns.

F. Catalyst Slurry and Solution Components

The catalyst of the invention can be added to the reaction system in the form of a slurry or a solution or a combination of slurry and solution. In one embodiment, the catalyst in slurry form and includes an activator and a support, or a supported activator. In another embodiment, the catalyst slurry includes fumed silica. In another embodiment, the slurry includes a catalyst compound in addition to the activator and the support and/or the supported activator. In one embodiment, the catalyst compound in the slurry is supported.

In another embodiment, the slurry includes one or more activator(s) and support(s) and/or supported activator(s) and/or one or more catalyst compound(s). For example, the slurry may include two or more activators (such as a supported alumoxane and a modified alumoxane) and a catalyst compound, or the slurry may include a supported activator and more than one catalyst compounds. Preferably, the slurry comprises a supported activator and two catalyst compounds.

In another embodiment the slurry comprises supported activator and two different catalyst compounds, which may be added to the slurry separately or in combination.

In another embodiment the slurry, containing a supported alumoxane, is contacted with a catalyst compound, allowed to react, and thereafter the slurry is contacted with another catalyst compound. In another embodiment the slurry containing a supported alumoxane is contacted with two catalyst compounds at the same time, and allowed to react.

In another embodiment the molar ratio of metal in the activator to metal in the catalyst compound in the slurry is 1000:1 to 0.5:1, preferably 300:1 to 1:1, more preferably 150:1 to 1:1.

In another embodiment the slurry contains a support material which may be any inert particulate carrier material known in the art, including, but not limited to, silica, fumed silica, alumina, clay, talc or other support materials such as disclosed above. In a preferred embodiment, the slurry contains a supported activator, such as those disclosed above, preferably methyl alumoxane and/or modified methyl alumoxane on a support of silica.

A catalyst slurry can be prepared by suspending the catalyst components, preferably the support, the activator and optional catalyst compounds in a liquid diluent. The liquid diluent is typically an alkane having from 3 to 60 carbon atoms, preferably having from 5 to 20 carbon atoms, preferably a branched alkane, or an organic composition such as mineral oil or silicone oil. The diluent employed is preferably liquid under the conditions of polymerization and relatively inert. The concentration of the components in the slurry is controlled such that a desired ratio of catalyst compound(s) to activator, and/or catalyst compound to catalyst compound is fed into the reactor.

Typically, as a slurry, the catalyst compound and the support and activator, or supported activator, and the slurry diluent are allowed to contact each other for a time sufficient for at least 50% of the catalyst compounds to be deposited into or on the support, preferably at least 70%, preferably at least 75%, preferably at least 80%, more preferably at least 90%, preferably at least 95%, preferably at least 99%. In an embodiment, the slurry is prepared prior to its use in the catalyst feed system. Times allowed for mixing are up to 10 hours, typically up to 6 hours, more typically 4 to 6 hours. In one embodiment of this invention a catalyst compound will be considered to be in or on the support if the concentration of the catalyst compound in the liquid portion of the slurry is reduced over time after adding the catalyst compound to the slurry. Concentration of the catalyst compound in the liquid diluent may be measured for example, by inductively coupled plasma spectroscopy (ICPS), or by ultraviolet (UV) spectroscopy, after standardization with a calibration curve prepared at the appropriate concentration range, as is known in the art. Thus for example, 70% of a catalyst compound will be considered to have deposited in or on a support if the concentration of the catalyst compound in the liquid (not including the support) is reduced by 70% from its initial concentration.

In one embodiment, the catalyst compounds are added to the slurry as a solution, slurry, or powder. The slurry may be prepared prior to its use in the polymerization process of the invention or it may be prepared in-line.

In one embodiment, the slurry is prepared by combining the catalyst components, such as for example the catalyst or supported catalyst and the support and activator or supported activator, all at once. In another embodiment, the slurry is prepared by first adding a support material, then adding the combination of a catalyst and an activator component.

In another embodiment the slurry comprises a supported activator and at least one catalyst compound where the catalyst compound is combined with the slurry as a solution. A preferred solvent is mineral oil.

In a another embodiment, alumoxane, preferably methyl alumoxane or modified methyl alumoxane, is combined with a support such as calcined silica or fumed silica to form a supported activator, the supported activator is then dispersed in a liquid, such as degassed mineral oil, and then one or more catalyst compounds are added to the dispersion and mixed to form the catalyst component slurry. The catalyst compounds are preferably added to the dispersion as a solid, powder, solution or a slurry, preferably a slurry of mineral oil. If more than one catalyst compound is added to the dispersion, the catalyst compounds can be added sequentially, or at the same time.

In another embodiment the catalyst compound is added to the slurry in solid or powder form. In a preferred embodiment, a Group 15 containing catalyst compound is added to the slurry in powder or solid form. In another preferred embodiment, [(2,4,6-Me$_3$C$_6$H$_2$)NCH$_2$CH$_2$]$_2$NHZrBz$_2$ and or [(2,4,6-Me$_3$C$_6$H$_2$)NCH$_2$CH$_2$]$_2$NHHfBz$_2$ is added to the slurry as a powder.

In a preferred embodiment the slurry comprises mineral oil and has a viscosity of about 130 to about 2000 cP at 20° C., more preferably about 180 to about 1500 cP at 20° C. and even more preferably about 200 to about 800 cP at 20° C. as measured with a Brookfield model LVDV-III Rheometer housed in a nitrogen purged drybox (in such a manner that the atmosphere is substantially free of moisture and oxygen, i.e. less than several ppmv of each). The slurry can be made in a nitrogen purged drybox, and rolled in closed glass containers until immediately before the viscosity measurements are made, in order to ensure that it is fully suspended at the start of the trial.

In one embodiment, the slurry comprises a supported activator and one or more or a combination of the catalyst compound(s) described in Formula I to IX above.

In another embodiment, the slurry comprises a supported activator and one or more or a combination of the Group 15 catalyst compound(s) represented by Formula V or VI described above.

In another embodiment, the slurry comprises a supported activator and one or more or combination of the bulky ligand catalyst compound(s) represented by Formula I to IV described above.

In another embodiment, the slurry comprises supported activator, a Group 15 catalyst compound(s) represented by Formula V or VI described above, and a the bulky ligand catalyst compound(s) represented by Formula I to IV.

In another embodiment, the slurry comprises supported alumoxane and $[(2,4,6-Me_3C_6H_2)NCH_2CH_2]_2NH$ $MBz_2$ where M is a Group 4 metal, each Bz is a independently a benzyl group and Me is methyl.

In another embodiment, the slurry comprises a supported alumoxane, a Group 15 catalysts compound and one of the following: bis(n-propyl cyclopentadienyl)-$MX_2$, (pentamethylcyclopentadienyl)(n-propylcyclopentadienyl)$MX_2$, bis(indenyl)-$MX_2$, or (tetramethylcyclopentadienyl) (n-propyl cyclopentadienyl) $MX_2$, where M is zirconium, hafnium or titanium and X is chlorine, bromine, or fluorine.

In one embodiment, the catalyst is added to the reaction system as a solution that includes a catalyst compound. In another embodiment, the solution also includes an activator in addition to the catalyst compound.

The solution used in the process of this invention is typically prepared by dissolving the catalyst compound and optional activators in a liquid solvent. The liquid solvent is typically an alkane, such as a $C_5$ to $C_{30}$ alkane, preferably a $C_5$ to $C_{10}$ alkane. Cyclic alkanes such as cyclohexane and aromatic compounds such as toluene may also be used. In addition, mineral oil may be used as a solvent. The solution employed should be liquid under the conditions of polymerization and relatively inert. In one embodiment, the liquid utilized in the solution is different from the diluent used in the slurry. In another embodiment, the liquid utilized in the solution is the same as the diluent used in the slurry.

In a preferred embodiment the ratio of metal in the activator to metal in the catalyst compound in the solution is 1000:1 to 0.5:1, preferably 300:1 to 1:1, more preferably 150:1 to 1:1.

In a preferred embodiment, the activator and catalyst compound is present in the solution at up to about 90 wt %, preferably at up to about 50 wt %, preferably at up to about 20 wt %, preferably at up to about 10 wt %, more preferably at up to about 5 wt %, more preferably at less than 1 wt %, more preferably between 100 ppm and 1 wt % based upon the weight of the solvent and the activator or catalyst compound.

In one embodiment, the solution comprises any one of the catalyst compounds described in Formula I to IX above.

In another embodiment, the solution comprises a Group 15 catalyst compound represented by Formula V or VI described above.

In another embodiment, the solution comprises a bulky ligand catalyst compound represented by Formula I to IV described above.

In a preferred embodiment the solution comprises bis(n-propyl cyclopentadienyl)-$MX_2$, (pentamethylcyclopentadienyl)(n-propylcyclopentadienyl)$MX_2$, bis(indenyl)-$MX_2$, (tetramethylcyclopentadienyl) (n-propylcyclopentadienyl) $MX_2$, where M is a Group 4 metal, preferably zirconium, hafnium or titanium and X is chlorine, bromine, or fluorine.

In the polymerization process of the invention, any catalyst solutions may be combined with any catalyst containing slurry. In addition, more than one catalyst component may be utilized.

Ideally, the fluorocarbon is inert to the polymerization reaction. By "inert to the polymerization reaction" is meant that the fluorocarbon does not react chemically with the, monomers, catalyst system or the catalyst system components. (This is not to say that the physical environment provided by an FC's does not influence the polymerization reactions, in fact, it may do so to some extent, such as affecting activity rates. However, it is meant to say that the FC's are not present as part of the catalyst system.)

VI. Monomers

Polymers produced according to this invention are olefin polymers or "polyolefins". By olefin polymers is meant that at least 75 mole % of the polymer is made of hydrocarbon monomers, preferably at least 80 mole %, preferably at least 85 mole %, preferably at least 90 mole %, preferably at least 95 mole %, preferably at least 99 mole %. In a particularly preferred embodiment, the polymers are 100 mole % hydrocarbon monomer. Hydrocarbon monomers are monomers made up of only carbon and hydrogen. In another embodiment of the invention up to 25 mol % of the polyolefin is derived from heteroatom containing monomers. Heteroatom containing monomers are hydrocarbon monomers where one or more hydrogen atoms have been replaced by a heteroatom. In a preferred embodiment, the heteroatom is selected from the group consisting of chlorine, bromine, oxygen, nitrogen, silicon and sulfur, preferably the heteroatom is selected from the group consisting of oxygen, nitrogen, silicon and sulfur, preferably the heteroatom is selected from the group consisting of oxygen and nitrogen, preferably oxygen. In a preferred embodiment, the heteroatom is not fluorine. In another embodiment of the invention, the monomers to be polymerized are not fluoromonomers. Fluoromonomers are defined to be hydrocarbon monomers where at least one hydrogen atom has been replaced by a fluorine atom. In another embodiment of the invention, the monomers to be polymerized are not halomonomers. (By halomonomer is meant a hydrocarbon monomer where at least one hydrogen atom is replaced by a halogen.) In another embodiment of the invention, the monomers to be polymerized are not vinyl aromatic hydrocarbons. In another embodiment of the invention, the monomers to be polymerized are preferably aliphatic or alicyclic hydrocarbons. (as defined under "Hydrocarbon" in Hawley's Condensed Chemical Dictionary, 13th edition, R. J. Lewis ed., John Wiley and Sons, New York, 1997. In another embodiment of the invention, the monomers to be polymerized are preferably linear or branched alpha-olefins, preferably C2 to C40 linear or branched alpha-olefins, preferably C2 to C20 linear or branched alpha-olefins, preferably ethylene, propylene, butene, pentene, hexene, heptene, octene, nonene, decene, undecene, dodecene, or mixtures thereof, more preferably ethylene, propylene, butene hexene and octene.

The processes described herein may be used in any type of polymerization process employing one or more monomers. Typical monomers include unsaturated hydrocarbons having from 2 to 30 carbon atoms, preferably 2 to 12 carbon atoms, and more preferably 2 to 8 carbon atoms. Useful monomers include linear, branched or cyclic olefins; linear branched or cyclic alpha olefins; linear, branched or cyclic diolefins; linear branched or cyclic alpha-omega olefins; linear, branched or cyclic polyenes; linear branched or cyclic alpha olefins. Particularly preferred monomers include one or more of ethylene, propylene, butene-1, pentene-1,4-methyl-pentene-1, hexene-1, octene-1, decene-1,3-methyl-pentene-1, norbornene, norbornadiene, 3,5,5-trimethyl-1-hexene, 5-ethyl-1-nonene, vinyl norbornene, and ethylidene monomers.

Preferred cyclic containing monomers include aromatic-group-containing monomers containing up to 30 carbon atoms and non aromatic cyclic group containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment the polymer produced herein is an ethylene homopolymer or copolymer. In a particularly preferred embodiment, the process of this invention relates to the polymerization of ethylene and one or more $C_4$ to $C_{20}$ linear, branched or cyclic monomers, preferably $C_4$ to $C_{12}$ linear or branched alpha-olefins. In a preferred embodiment, the comonomer comprises at least one comonomer having from 3 to 8 carbon atoms, preferably 4 to 8 carbon atoms. Particularly, the comonomers are propylene, butene-1,4-methyl-pentene-1,3-methyl-pentene-, 1hexene-1 and octene-1, the most preferred being hexene-1, butene-1 and or octene-1.

In a preferred embodiment the polymer produced herein is a propylene homopolymer or copolymer. In a particularly preferred embodiment, the process of the invention relates to the polymerization of propylene and one or more $C_4$ to $C_{20}$ linear, branched or cyclic monomers, preferably $C_4$ to $C_{12}$ linear or branched alpha-olefins. In a preferred embodiment, the comonomer comprises at least one comonomer having from 2 to 8 carbon atoms, preferably 4 to 8 carbon atoms, preferably ethylene, butene-1, pentene, hexene-1, heptene-1, octene-1, nonene-1, decene-1, dodecene-1,4-methyl-pentene-1,3-methyl pentene-1,3,5,5-trimethyl-hexene-1, and the like. In some embodiments, ethylene is present at 5 mol % or less.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a preferred embodiment, the monomer is present in the polymer at 50 mole % to 99.9 mole %, more preferably 70 to 98 mole %, and more preferably 80 to 95 mole %. Comonomer(s) are present in the polymer at 0.1 mole % to 50 mole %, based upon the moles of all monomers present, more preferably 2 to 30 mole %, more preferably 5 to 20 mole %.

In another embodiment, the polymer produced herein comprises:

a first olefin monomer present at from 40 to 100 mole %, preferably 50 to 100 mole %, more preferably 60 to 100 mole %, and a second olefin monomer (a comonomer) present at from 0 to 60 mole %, preferably 0 to 30 mole %, more preferably 0 to 10 mole %, and optionally a third olefin monomer present at from 0 to 10 mole %, more preferably from 0 to 5 mole %, more preferably 0 to 3 mole %.

In a preferred embodiment the first olefin monomer comprises one or more of any $C_3$ to $C_8$ linear, branched or cyclic alpha-olefins, including propylene, 1-butene, (and all isomers thereof), 1-pentene (and all isomers thereof), 1-hexene (and all isomers thereof), 1-heptene (and all isomers thereof), and 1-octene (and all isomers thereof). Preferred monomers include propylene, 1-butene, 1-hexene, 1-octene, and the like.

In a preferred embodiment the second olefin monomer comprises one or more of any $C_2$ to $C_{40}$ linear, branched or cyclic alpha-olefins, including ethylene, propylene, 1-butene, 1-pentene, 1-hexene, 1-heptene, and 1-octene, 1-nonene, 1-decene, 1-undecene, 1-dodecene, 1-hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the third olefin monomer comprises one or more of any $C_2$ to $C_{40}$ linear, branched or cyclic alpha-olefins, including butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

VII. Processes

A. General Process Conditions and Reactor Systems

This invention pertains to any prepolymerization and/or polymerization process, and the process is suitably carried out over a wide range of temperatures and pressures. Such processes include, for example, solution, gas phase, slurry phase, medium pressure and high pressure processes or any combination thereof. Particularly preferred is gas phase or slurry phase polymerization of one or more olefins. In a particularly preferred embodiment, at least one of the olefins is ethylene or propylene.

The prepolymerization and/or polymerization process can be carried out in a batch or continuous process. By continuous is meant a system that operates (or is intended to operate) without interruption or cessation. For example a continuous process to produce a polymer would be one in which the reactants are continuously introduced into one or more reactors and polymer product is continually withdrawn. In a preferred embodiment any of the polymerization process described herein are a continuous process.

Polymerization processes according to this invention are carried out at any temperature or temperature range effective in carrying out the polymerization process. In general, effective temperatures range from about −80° C. to 350° C., preferably from about 0° C. to 200° C., more preferably from about 50° C. to 120° C. In another embodiment, the polymerization temperature is above room temperature (23° C.), preferably above 30° C., preferably above 50° C., preferably above 70° C.

Polymerization processes according to this invention are carried out at any pressure or pressure range effective in carrying out the polymerization process. The pressures employed may be in the range from 1 mm Hg (133 Pa) to about 3500 bar (350 MPa), preferably from 0.5 bar (50 kPa) to about 500 bar (50 MPa), more preferably from about 1 bar (100 kPa) to about 100 bar (10 MPa), and most preferably from about 5 bar to about 50 bar (5 MPa).

In one embodiment, the process of this invention is directed toward a solution, medium pressure, high pressure, slurry phase or gas phase polymerization process of one or more olefin monomers having from 2 to 30 carbon atoms, preferably 2 to 12 carbon atoms, and more preferably 2 to 8 carbon atoms. The invention is particularly well suited to the polymerization of one or more olefin monomers of ethylene, propylene, 1-butene, 1-pentene, 4-methyl-pentene-1,1-hexene, 1-octene and 1-decene.

In another preferred embodiment of the invention, ethylene is polymerized with a comonomer, the comonomer having at least one alpha-olefin having from 3 to 15 carbon atoms, preferably from 4 to 12 carbon atoms, and most preferably from 4 to 8 carbon atoms. Preferably the reaction is carried out in a gas phase process.

In another embodiment of the invention, ethylene or propylene is polymerized with at least two different comonomers, optionally one of which may be a diene, to form a terpolymer.

In yet another embodiment, the mole ratio of comonomer to ethylene, $C_x/C_2$, where $C_x$ is the amount of comonomer and $C_2$ is the amount of ethylene, is from about 0.001 to 0.4 and more preferably from about 0.02 to 0.2.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene catalysts as described in U.S. Pat. Nos. 5,296,434 and 5,278,264, both of which are herein incorporated by reference.

Another preferred process of the invention is where the process, preferably a slurry or gas phase process is operated in the presence of a bulky ligand metallocene catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. Nos. 5,712,352 and 5,763,543, which are herein fully incorporated by reference.

In one embodiment of the invention, olefin(s), preferably $C_2$ to $C_{30}$ olefin(s) or alpha-olefin(s), preferably ethylene or propylene or combinations thereof are prepolymerized in the presence of the metallocene catalyst systems of the invention described above prior to the main polymerization. In one embodiment, the prepolymerization process is carried out in a gas, solution or slurry phase at effective prepolymerization temperatures and pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578 and European publication EP-B-0279 863 and PCT Publication WO 97/44371 all of which are herein fully incorporated by reference.

In one embodiment, the polymerization is carried out where the catalyst, monomer, and diluent are present in a single phase. In a preferred embodiment, polymerization is carried out as a continuous polymerization process in which catalyst, monomer, and diluent are present in a single phase. By continuous is meant a system that operates (or is intended to operate) without interruption or cessation. For example a continuous process to produce a polymer would be one where the reactants are continuously introduced into one or more reactors and polymer product is continually withdrawn.

The reactor used in the polymerization process of this invention, will contain sufficient amounts of the catalyst system effective to catalyze the polymerization of the monomer containing feed-stream such that a sufficient amount of polymer having desired characteristics is produced. The feed stream in one embodiment contains a total monomer concentration greater than 5 wt % (based on the total weight of the monomers, diluent, and catalyst system), preferably greater than 15 wt %, greater than 30 wt % in another embodiment. In yet another embodiment, the feed-stream will contain from 5 wt % to 50 wt % monomer concentration based on the total weight of monomer, diluent, and catalyst system.

In one embodiment of the invention, hydrogen is added to the reactor for molecular weight control. As is well known to those skilled in the art, increased concentrations of hydrogen relative to the concentration of monomer(s) in the reactor cause the production of polymer of lower number average and weight average molecular weights.

In one embodiment of the invention, a liquid process is employed, which comprises contacting olefin monomers with polymerization catalyst in an optional solvent and allowing the monomers to react for a sufficient time to produce the desired polymers. Hydrocarbon solvents suitable for the process include aliphatic and aromatic solvents. Alkanes, such as hexane, pentane, isopentane, and octane, are preferred.

B. Gas Phase Embodiments

One embodiment of the invention incorporates the use of a gas phase polymerization process. Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. See, for example, U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.

The reactor pressure in a gas phase process may vary from about 100 psig (690 kPa) to about 600 psig (4138 kPa), preferably in the range of from about 200 psig (1379 kPa) to about 400 psig (2759 kPa), more preferably in the range of from about 250 psig (1724 kPa) to about 350 psig (2414 kPa).

The productivity of the catalyst or catalyst system in a gas phase system is influenced by the partial pressure of the main monomer. The preferred mole percent of the main monomer, ethylene or propylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In a preferred embodiment, the reactor and processes utilized in the invention are capable of producing greater than 500 lbs of polymer per hour (227 kg/hr) to about 200,000 lbs/hr (90,900 kg/hr) or higher of polymer, preferably greater than 1000 lbs/hr (455 kg/hr), more preferably greater than 10,000 lbs/hr (4540 kg/hr), even more preferably greater than 25,000 lbs/hr (11,300 kg/hr), still more preferably greater than 35,000 lbs/hr (15,900 kg/hr), still even more preferably greater than 50,000 lbs/hr (22,700 kg/hr) and most preferably greater than 65,000 lbs/hr (29,000 kg/hr) to greater than 100,000 lbs/hr (45,500 kg/hr).

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

C. Slurry Process Embodiments

One embodiment of the invention incorporates the use of a slurry phase polymerization process, preferably as a continuous polymerization process. The slurry polymerization process is preferably carried out at pressures in the range of from about 1 to about 100 atmospheres, preferably in the range of from 1 to 50 atmospheres. Operating temperatures are generally in the range of 0° C. to about 120° C.

In one embodiment of the slurry process, the monomers, catalyst(s), and initiator(s) are miscible in the diluent or diluent mixture, i.e., constitute a single phase, while the polymer precipitates from the diluent with good separation from the diluent. In one embodiment, a solvent or co-diluent is added to the reaction process. In a particular embodiment, an alkane having from 3 to 7 carbon atoms, preferably a branched alkane, is added. Preferred alkanes include isobutane and isohexane.

A preferred polymerization technique of the invention is referred to as a particle form polymerization, which is essentially a slurry process utilizing a supported catalyst wherein the temperature is kept below the temperature at which the polymer goes into solution. Such technique is well known in the art, and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. Nos. 4,613,484 and 5,986,021, which are herein fully incorporated by reference.

In one embodiment, the reactor used in the slurry process of the invention is capable of producing greater than 500 lbs of polymer per hour (227 kg/hr) to about 200,000 lbs/hr (90,900 kg/hr) or higher of polymer, preferably greater than 1000 lbs/hr (455 kg/hr), more preferably greater than 10,000 lbs/hr (4540 kg/hr), even more preferably greater than 25,000 lbs/hr (11,300 kg/hr), still more preferably greater than 35,000 lbs/hr (15,900 kg/hr), still even more preferably greater than 50,000 lbs/hr (22,700 kg/hr) and most preferably greater than 65,000 lbs/hr (29,000 kg/hr) to greater than 100,000 lbs/hr (45,500 kg/hr).

In one embodiment, polymer granules and supported catalyst particles are present as solid particles in the slurry reactor, and the slurry diluent is a hydrofluorocarbon, one or more hydrocarbons, or mixtures thereof. In one embodiment, the concentration of solid particles in the slurry is equal to or greater than 10 vol %. In another embodiment, the solid particles are present in the slurry at a concentration equal to or greater than 25 vol %. In yet another embodiment, the solid particles are present in the slurry at a concentration less than or equal to 75 vol %. In yet another embodiment, the solid particles are present in the slurry at concentrations ranging from 1 to 70 vol %; from 5 to 70 vol %; from 10 to 70 vol %; from 15 to 70 vol %; from 20 to 70 vol %; from 25 to 70 vol %; from 30 to 70 vol %; or from 40 to 70 vol %.

D. Solution Process

In one embodiment, the process of this invention is carried out as a solution polymerization process. Generally, the solution process involves polymerization in a continuous reactor in which the starting monomer(s) and catalyst materials supplied and the polymer formed, are agitated to reduce or avoid concentration gradients. Suitable processes operate above the melting point of the polymers at high pressures, from 1 bar (100 kPa) to 3000 bar (300 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg (133 Pa) to 2500 bar (250 MPa), preferably from 0.1 bar (10 kPa) to 1600 bar (160 MPa), most preferably from 1.0 bar (100 kPa) to 500 bar (50 MPa).

Examples of solution processes are described in U.S. Pat. Nos. 4,271,060, 5,001,205, 5,236,998, 5,589,555 and 5,977,251 and PCT WO 99/32525 and PCT WO 99/40130, which are fully incorporated herein by reference.

E. Medium and High Pressure Polymerization

The polymerization process of this invention can also be carried out at medium or high pressures. For medium pressure processes, the temperature at which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied from 100 to 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

In high pressure processes, particularly for the polymerization of ethylene alone or in combination with $C_3$ to $C_{10}$ alpha-olefins, and optionally other copolymerizable olefins, the temperature of the medium in which the polymerization reaction occurs is at least 120° C. and preferably above 140° C. and may range to 350° C., but below the decomposition temperature of the polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. patent applications 60/431,185 filed Dec. 5, 2002; 60/431,077, filed Dec. 5, 2002; and 60/412,541, filed Sep. 20, 2002.

F. Reactors and Reactor Systems

The invention may be practiced in any type of polymerization reactor system, such as continuous and batch reaction systems suitable for carrying out any one or more of the solution, gas phase, slurry phase, medium pressure or high pressure processes. In one embodiment, the invention is practiced in a fluidized bed reactor, loop reactor, plug flow reactor and/or stirred tank reactor. In a particular embodiment, this invention is practiced in a "butyl reactor." Other examples of reactors include any reactor selected from the group consisting of a continuous flow reactor, stirred tank reactor, plug flow reactor, moving belt reactor, drum reactor, jet reactor, nozzle reactor, tubular reactor, autorefrigerated boiling-pool reactor or any combination thereof.

In another aspect, heat can be removed from the reactor system by use of heat transfer surfaces, such as in a tubular reactor where a coolant is on one side of the tube and the polymerizing mixture is on the other side. Heat may also be removed by evaporating the polymerizing mixture, such as may be found in an autorefrigerated boiling pool type reactor. Another example, is a plug flow reactor where a portion of the polymerizing mixture is evaporated as the mixture proceeds through the reactor. Another example is where heat is removed in a plug flow reactor through surface heat transfer using coolant on the other side of a heat transfer surface. Another example would be a reactor where polymerization takes place on a moving belt or drum where the diluent/monomer/catalyst mixture is sprayed onto the belt or drum and heat is removed by evaporation of the diluent as the reaction proceeds. In addition heat may be removed in such reactors by surface heat transfer (such as where the coolant is present on the inside of the drum or under the belt and the polymer is produced on the other side of the belt or drum). Another type of reactor is a jet or nozzle reactor. These reactors have a short residence time where the monomer, diluent and catalyst system are combined in the jet or nozzle and the polymerization occurs as the mixture passes through the nozzle at high velocity.

One or more reactors in series or in parallel may be used in this invention. Catalyst component(s) (and any activator employed) may be delivered as a solution or slurry, either separately to the reactor, activated in-line just prior to the reactor, or preactivated and pumped as an activated solution or slurry to the reactor. A preferred operation is two solutions activated in-line. For information on methods to introduce multiple catalysts into reactors, see U.S. Pat. No. 6,399,722 and WO 01/30861 A1. While these reference may emphasize gas phase reactors, the techniques described are equally applicable to other types of reactors, including continuous stirred tank reactors, slurry loop reactors and the like. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst component may also be added to both reactors, with one component being added to a first reactor and other components added to other reactors.

In one embodiment, a continuous flow stirred tank-type reactor is used. The reactor is generally fitted with an efficient agitation means, such as a turbo-mixer or impeller(s), an external cooling jacket and/or internal cooling tubes and/or coils, or other means of removing the heat of polymerization to maintain the desired reaction temperature, inlet means (such as inlet pipes) for monomers, diluents and catalysts (combined or separately), temperature sensing means, and an effluent overflow or outflow pipe which withdraws polymer, diluent and unreacted monomers among other things, to a holding drum or quench tank. Preferably, the reactor is purged of air and moisture. One skilled in the art will recognize proper assembly and operation. The reactors are preferably designed to deliver good mixing of the catalyst and monomers within the reactor, good turbulence across or within the heat transfer tubes or coils, and enough fluid flow throughout the reaction volume to avoid excessive polymer accumulation or separation from the diluent.

In another embodiment of the invention, a reactor capable of performing a continuous slurry process, such as disclosed in U.S. Pat. No. 5,417,930, herein incorporated by reference, is used. A reactor pump impeller is employed in the reactor and can be of the up-pumping variety or the down-pumping variety.

The order of contacting the monomer feed-stream, catalyst, initiator, and diluent may be variable. In one embodiment, the initiator and catalyst are pre-complexed by mixing together in the selected diluent for a prescribed amount of time ranging from 0.01 second to 10 hours, and then is injected into a continuous reactor through a catalyst nozzle or injection apparatus. In yet another embodiment, catalyst and the initiator are added to the reactor separately. In another embodiment, the initiator is blended with the feed monomers before injection to the reactor. Desirably, the monomer is not contacted with the catalyst, or the catalyst combined with the initiator before entering the reactor.

VIII. Polymer Products

A. General Polymer Products

The polymers produced by the process of the invention can be used in a wide variety of products and end-use applications. The polymers produced by the process of the invention include linear low density polyethylene, elastomers, plastomers, high density polyethylenes, medium density polyethylenes, low density polyethylenes, multimodal or bimodal high molecular weight polyethylenes, polypropylene and polypropylene copolymers.

B. Density

The polymers produced according to this invention can be produced at any density suitable for the appropriate end use. In one embodiment, there can be produced ethylene based polymers having a density in the range of from 0.86 g/cc to 0.97 g/cc. For some applications, a density in the range of from 0.88 g/cc to 0.920 g/cc is preferred while in other applications, such as pipe, film and blow molding, a density in the range of from 0.930 g/cc to 0.965 g/cc is preferred. For low density polymers, such as for film applications, a density of 0.910 g/cc to 0.940 g/cc is preferred. Density is measured in accordance with ASTM method 1505.

C. Molecular Weight and Molecular Weight Distribution

The polymers produced by the process of the invention can be produced in a wide variety of molecular weights and molecular weight distributions. Molecular weights (weight average molecular weight (Mw) and number average molecular weight (Mn)) are preferably determined using a Waters 150 Size Exclusion Chromatograph (SEC) equipped with a differential refractive index detector (DRI), an online low angle light scattering (LALLS) detector and a viscometer (VIS). The details of the detector calibrations are described by T. Sun, P. Brant, R. R. Chance, and W. W. Graessley, *Macromolecules*, Volume 34, Number 19, 6812-6820, (2001), and are incorporated herein by reference.

In an embodiment of the invention, the polymers produced have a molecular weight distribution (MWD), which is defined as a ratio of weight average molecular weight to number average molecular weight ($MWD=M_w/M_n$), of greater than 1.5, preferably from 1.5 to about 70. In some embodiments, the polymer has a $M_w/M_n$ of at least 2, preferably from about 2 to 60, while in other embodiments the polymer produced has a $M_w/M_n$ of at least 5, preferably from about 5 to 50. In an embodiment, the polymer of the invention has a narrow molecular weight distribution and a broad composition distribution, and vice-versa, such as those polymers described in U.S. Pat. No. 5,798,427, incorporated herein by reference.

In another embodiment, the polyolefin produced has at least two species of molecular weights. Preferably, both species are present at greater than 20 wt %, based upon weight average molecular weight.

D. Bi- or Multi-Modal Polymers

In another embodiment of this invention the polymer produced is bi- or multi-modal (on the SEC graph). By bi- or multi-modal means that the SEC graph of the polymer has two or more positive slopes, two or more negative slopes, and three or more inflection points (an inflection point is that point where the second derivative of the curve is equal to zero) or the graph has at least has one positive slope, one negative slope, one inflection point and a change in the positive and or negative slope greater than 20% of the slope before the change.

In one embodiment, the SEC graph has one positive slope, one negative slope, one inflection point and an Mw/Mn of 10 or more, preferably 15 or more, more preferably 20 or more. The columns are calibrated by running a series of narrow polystyrene standards and the molecular weights were calculated using Mark Houwink coefficients for the polymer in question.

In a particular embodiment, bi-modal polymers are produced having a density of 0.93 to 0.96 g/cc, an MI ($I_2$) of 0.03-0.10 g/10 min, an FI ($I_{21}$) of 4-12 g/10 min, an MFR ($I_{21}/I_2$) of 80-180, an overall Mw of 200,000 to 400,000, an overall Mn of 5,000-10,000 and an Mw/Mn of 20-50. Preferably, the particular polymers have a low molecular weight fraction (~500-~50,000) having a density of 0.935-0.975 g/cc and a high molecular weight fraction (~50,000-~8,000,000) having a density of 0.910-0.950 g/cc. These polymers are particularly useful for film and pipe, especially, for PE-100 pipe applications. The molecular weight distributions (MWDs), as obtained from size exclusion chromatography (SEC), can be deconvoluted using a bimodal fitting program. In one embodiment, the polymer has weight ratio of the high molecular weight (HMW) fraction to the low molecular weight (LMW) fraction of ranging from 20-80 to 80-20, more preferably from 30-70 to 70-30, and even more preferably from 40-60 to 60-40. A higher wt % of HMW than LMW wt % is preferred. The SEC curve can be further analyzed to give percent of wt %>1 MM, which is the weight percent of the total MWD that has a molecular weight greater than 1 million, and wt %>100 K, which is the weight percent of the total MWD that is greater than 100,000 in molecular weight. The weight percent ratio is simply wt %>1 MM divided by wt %>100 K. 100,000 was used as an approximate means of dividing the total MWD into a HMW (high molecular weight) and LMW (low molecular weight) region. This ratio gives a simple but sensitive indication of the relative amount of the very high molecular weight species in the HMW region of the MWD. The preferred embodiment of the polymer has the preferred range of weight percent ratio (WPR), higher than 10 but less than 30, preferably higher than 15 but less than 25.

In another embodiment, a bimodal molecular weight polymer is produced having a density of 0.93 to 0.97 g/cc, an MI ($I_2$) of 0.02-0.5 g/10 min, an FI ($I_{21}$) of 10-40 g/10 min, an MFR ($I_{21}/I_2$) of 50-300, an Mw of 100,000 to 500,000, an Mn of 8,000-20,000 and an Mw/Mn of 10-40. These polymers are particularly useful for blow molding applications. These bimodal polymers exhibit high Bent Strip ESCR (environmental stress crack resistance) performance, which far exceeds the performance of unimodal HDPE. Also, the blow molded bottles trim easier and typically have an opaque finish, which is preferred over a translucent finish of unimodal HDPE.

E. Composition Distribution Breadth Index

The polymers of the invention may have a narrow or broad composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference. In some embodiments the polymer produced may have a CDBI of 80% or more or may have a CDBI of 50% or less.

In one embodiment, the polymers of the invention have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, polymers produced using this invention have a CDBI less than 50%, more preferably less than 40%, and most preferably less than 30%.

F. Melt Index

The polymers produced by the process of the invention can be produced according to a desired or predetermined melt index, depending upon desired end use. In one embodiment, the polymers have a melt index (MI) or ($I_2$), as measured by ASTM-D-1238-E, in the range from 0.01 dg/min to 1000 dg/min, more preferably from about 0.01 dg/min to about 100 dg/min, even more preferably from about 0.01 dg/min to about 50 dg/min, and most preferably from about 0.1 dg/min to about 10 dg/min.

In another embodiment of the invention, the polymers have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio of from preferably greater than 25, more preferably greater than 30, even more preferably greater that 40, still even more preferably greater than 50 and most preferably greater than 65. In another embodiment, the polymer of the invention has a narrow molecular weight distribution and a broad composition distribution or vice-versa. Examples include those polymers described in U.S. Pat. No. 5,798,427, the description of which is incorporated herein by reference.

G. Tacticity

The term "tacticity" refers to the stereochemical configuration of a polymer, and the properties of a polymer having side chains are affected by its tacticity. For example, adjacent monomer units having side chains can have either like or opposite configuration. If all monomer units have like configuration, the polymer is "isotactic." If adjacent monomer units have an alternating configuration, and this alternating configuration continues along the entire polymer chain, the polymer is "syndiotactic." If the configuration of monomer units is random, the polymer is "atactic." When two contiguous monomer units, a "diad," have the same configuration, the diad is called isotactic or "meso" (m). When the monomer units have opposite configuration, the diad is called "racemic" (r). For three adjacent monomer units, a "triad," there are three possibilities. If the three adjacent monomer units have the same configuration, the triad is designated mm. An rr triad has the middle monomer unit having an opposite configuration from either neighbor. If two adjacent monomer units have the same configuration and it is different from the third monomer, the triad is designated as having mr tacticity. For five contiguous monomer units, a "pentad," there are ten possibilities: mmmm, mmmr, rmmr, mmrr, mrmm, rmrr, mmrr, rrrrr rrr, and mrrm. A completely syndiotactic polymer would have all rrrr pentads, while a completely isotactic polymer would have all mmmm pentads. The configuration can be determined by $^{13}C$ nuclear magnetic resonance spectroscopy as described in *Macromolecules* 8 687 (1975) and in *Macromolecules* 6 925 (1973) and references cited therein. For more information on polymer stereochemistry, see G. Odian, *Principles of Polymerization,* 2nd edition, pages 568-580 (1981).

Propylene based polymers can be produced using the process of this invention at various levels of tacticity. Examples of such polymers include atactic polypropylene, isotactic polypropylene, hemi-isotactic and syndiotactic polypropylene or mixtures thereof produced by using two or more different catalysts in the practice of this invention. Other propylene polymers include propylene block or impact copolymers. Propylene polymers of these types are well known in the art, see for example U.S. Pat. Nos. 4,794,096, 3,248,455, 4,376,851, 5,036,034 and 5,459,117, all of which are herein incorporated by reference.

In one embodiment of the invention, the polymer is polypropylene that is highly isotactic, readily forms a crystalline structure and has excellent chemical and heat resistance. In another embodiment, the polypropylene made by the process of the invention is highly syndiotactic. In yet another embodiment, the polypropylene made by the process of the invention is characterized in that it has low levels of isotacticity and/or low levels of syndiotacticity. In a particular embodiment, the percent of pentads having mmmm configuration is less than 40%, preferably more than 2%, and more preferably less than 30%. In yet another particular embodiment, the percent of pentads having rrrr is less than 75%, preferably more than 5% and more preferably less than 50%. At lower levels of syndiotacticity and isotacticity, the polymer is predominantly or even completely amorphous, generally has no melting point, is generally transparent and flexible, and has good elastic properties.

H. Polymer Blends

The polymers of the invention may be blended and/or coextruded with any other polymer. Non-limiting examples of other polymers include linear low density polyethylenes produced via conventional Ziegler-Natta and/or bulky ligand metallocene catalysis, elastomers, plastomers, high pressure low density polyethylene, high density polyethylenes, polypropylenes and the like.

I. Appearance

The films produced using the polymers of this invention have good appearance properties. In one embodiment, the films have a low gel content and/or have good haze and gloss. In a preferred embodiment, a 1 mil (1.0 mil=0.25 μm) film is produced that has a 45° gloss of 7 or more, preferably 8 or more, as measured by ASTM D 2475. In a preferred embodiment the 1 mil film (1.0 mil=25 μm) has a haze of 75 of less, preferably 70 or less as measured by ASTM D 1003, condition A.

J. Articles

Polymers produced by the process of the invention and blends thereof are useful in producing any variety of articles. For example, the polymers are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

The films may be formed by any of the conventional techniques known in the art including extrusion, co-extrusion, lamination, blowing and casting. The film may be obtained by the flat film or tubular process which may be followed by orientation in a uniaxial direction or in two mutually perpendicular directions in the plane of the film to the same or different extents. Orientation may be to the same extent in both directions or may be to different extents. Particularly preferred methods to form the polymers into films include extrusion or coextrusion on a blown or cast film line.

In another embodiment, the polymer of the invention is made into a film by methods known in the art. For film applications, the polymers of the invention have an $I_{21}$ value of from about 2 to about 100 dg/min, preferably from about 2 to about 50 dg/min, and more preferably from about 2 to about 30 dg/min. $I_{21}$ is measured by ASTM Method D 1238.

In another embodiment, the polymer of the invention is made into a molded article by methods known in the art, for example, by blow molding and injection-stretch molding. For molded applications, the polymers of the invention have a $I_{21}$ of from about 20 dg/min to about 50 dg/min and preferably from about 35 dg/min to about 45 dg/min.

In another embodiment, the polymer of the invention is made into a pipe by methods known in the art. For pipe applications, the polymers of the invention have a $I_{21}$ of from about 2 to about 10 dg/min and preferably from about 2 to about 8 dg/min. In another embodiment, the pipe of the invention satisfies ISO qualifications. In another embodiment, the present invention is used to make polyethylene pipe having a predicted S-4 $T_c$ for 110 mm pipe of less than −5° C., preferably of less than −15° C. and more preferably less than −40° C. (ISO DIS 13477/ASTM F1589).

In another embodiment, the polymer has an extrusion rate of greater than about 17 lbs/hour/inch of die circumference and preferably greater than about 20 lbs/hour/inch of die circumference and more preferably greater than about 22 lbs/hour/inch of die circumference.

The objects produced (such as films, pipes, etc.) may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, $BaSO_4$, diatomaceous earth, wax, carbon black, flame retarding additives, low molecular weight resins, hydrocarbon resins, glass beads and the like. The additives may be present in the typically effective amounts well known in the art, such as 0.001 weight % to 10 weight %.

The polymers of the invention may be blended and/or coextruded with any other polymer. Non-limiting examples of other polymers include linear low density polyethylenes produced via conventional Ziegler-Natta and/or bulky ligand metallocene catalysis, elastomers, plastomers, high pressure low density polyethylene, high density polyethylenes, polypropylenes and the like.

IX. Product Recovery

Polymer product that leaves the reactor unit of the reaction system contains entrained material that should be separated from the polymer. Included in this polymer product are unreacted monomers and undesirable hydrocarbon by-products of the reaction process. Also included are any diluent and/or solvent materials that are not reactive to form desirable polymer, and are especially problematic with regard to removal and/or recovery.

A substantial portion (i.e., a majority) of the polymer product is separated from the non-polymer product by sending product effluent from the polymer reactor to a polymer recovery system. The polymer recovery system is operated by controlling a variety of parameters including temperature, pressure, vapor-liquid separation systems, and purge systems or vessels.

In one embodiment, the polymer recovery system incorporates the use of an inert gas to purge or scrub out undesirable entrained material from the polymer product. The inert gas is a composition that is substantially non-reactive with the polymer product, and can be used in sufficient quantity as a driving force to separate the non-polymer components from the polymer product. Examples of useful inert gases include air and nitrogen.

In a particular embodiment, polymer associated with entrained materials such as unreacted monomer, hydrocarbon by-product and diluent such as hydrofluorocarbon is recovered from a polymerization reaction process and sent to a polymer recovery system. Preferably, the polymer recovery system includes a purge system or vessel, more preferably a purge bin, and the polymer and associated entrained materials are sent to the purge system. The inert gas composition is then input into the purge system to purge or drive out the entrained materials, thereby forming a purge stream, which is recovered from the purge system.

Entrained, non-polymer product material that is separated and recovered as a purge stream from the polymer product is preferably further separated into component fractions or a plurality of streams and each fraction or stream stored, recycled or vented from the system as appropriate. It is preferred that diluent and unreacted monomer be separated and returned to the reactor. These streams can be separated and recovered as individual streams or as a combined stream. If in inert gas is used in the recovery system, it is preferred that the inert gas also be separated, preferably as an individual stream, and recovered for reuse in the polymer recovery system and/or in the reaction portion of the polymerization system.

In one embodiment, the effluent from the polymerization reactor is flashed in a first flash to vaporize from about 50% to about 100% of the liquid medium to produce concentrated polymer effluent and vaporized liquid. Flashing can be accomplished by reducing pressure or by heating. Preferably, the vapor obtained in the first flash is condensed, more preferably the vapor is condensed without compression, and most preferably is condensed by heat exchange. Preferably, the first flash is operated at from about 140 psia to about 315 psia.

In another embodiment, polymer solids are discharged from a first flash to a second flash through a seal chamber. The seal chamber preferably is of sufficient dimension such as to maintain a volume of polymer solids/slurry in the seal chamber sufficient to maintain a pressure seal.

In another embodiment, concentrated polymer effluent and vaporized liquid are continuously separated. In a preferred aspect, the concentrated polymer effluent slurry is flashed in a second flash to vaporize liquid.

In one embodiment of the invention, the polymerization effluent from the polymerization reactor is heated and then sent to a flash operation. Preferably, the polymerization effluent is heated to a temperature below the fusion temperature of the polymer. The quantity of heat supplied to the polymerization effluent is preferably at least equal to that quantity of heat which equals the heat of vaporization of the liquid medium which is to be flashed.

The polymer solids can be separated by any appropriate physical means as well. One non-limiting example is to separate the polymer solids from the diluent using a centrifuge apparatus.

In another embodiment, activated carbon is used to remove the fluorocarbon(s) from the polymer streams, hydrocarbon streams and/or the waste streams. When using fluorocarbons in a process (such as a polymerization process) it is useful to prevent the escape of the fluorocarbons to the atmosphere. It is also useful to prevent the passage of fluorocarbons to the flare or other combustion process. Specifically, in some embodiments, activated carbon is used to remove the fluorocarbons from a gas or liquid process stream.

In another embodiment, the activated carbon would be used as the absorbent material in a Pressure Swing Adsorption (PSA) process. A PSA process employs at least two separate adsorption columns. One column operates as the active column, adsorbing material from the flow stream while the other operates off-line (at reduced pressure) in the "regeneration" mode. When the adsorption capacity of the active column is reached, the role of the columns is reversed. The alternating cycles of this process provide an effectively continuous flow path through the system, and a continuous removal of certain components from the flow stream (i.e. those components that are strongly adsorbed by the activated carbon, such as fluorocarbons). In another preferred embodiment, when using the activated carbon for removal of fluorocarbons from a process stream, a PSA system of a given size could operated at a reduced cycle frequency for improved reliability and reduced mechanical wear on the switching valve components as compared to a process stream of hydrocarbons without fluorocarbons. In another preferred embodiment, a PSA system could be designed with smaller sized columns for reduced cost when using the activated carbon for removal of fluorocarbons from a process stream as compared to a process stream of hydrocarbons without fluorocarbon.

In an alternative embodiment, the activated carbon is used as a safety "guard bed" downstream of a primary separation system. The purpose of this guard bed would be to capture any fluorocarbon material that may bypass the primary separation system. In this case, the advantages provided by the activated carbon would be similar to that described above with PSA. The size (and cost) of the guard bed could be reduced significantly.

EXAMPLES

Example 1

A first cylinder of HFC-236fa (1,1,1,3,3,3-hexafluoropropane) was obtained and the HFC was treated by passing through a progression of 3A molecular sieve, 13X molecular sieve, Selexsorb CD and Oxyclear. Compound analysis of the HFC was performed using a HP6890 GC/MSD with two-dimensional approach. The GC columns used a Varian LowOx (pre-separates oxygenates from fluorocarbons) and a Restek RTX-200. Cryogenic conditions were not necessary.

The instrument parameters for the analysis were as follows:

Column: Varian LowOx (10 m, 0.53 mm ID; Restek RTX-200 (30 m, 0.32 mm ID, 1 μm df))

Injector: 250° C., Split 40:1, He carrier, Total flow at 26.2 ml/minute, 4.0 psi head pressure at 35° C., 0.5 μL sample injection MSD: SCAN Mode, Source Temp. 230° C., Quad Temp. 150° C.

Oven: Initial temperature of 35° C. held for 5 minutes; temperature increased at 5° C./min from 35° C. to 130° C. Temperature increased at 20° C./min to 200° C. and held for 6 minutes. Temperature increased at 10° C./min to 250° C. and held for 5 minutes.

Compounds detected in the GC/MSD system were not individually calibrated so the quantities were reported as part per million area (ppma). For example, if a single compound had a measured peak area of 0.01% of the total GC peak area for the entire composition tested, it was reported as having a concentration of 100 ppma.

The results are shown in Table 1.

TABLE 1

GC/MSD Analysis of HFC-236fa

| COMPOUND | Prior to Treatment (ppma) |
| --- | --- |
| Pentafluoro-2-Chloro-Propene | 10 |
| Pentafluoro-1-Propene | 31 |
| Hexafluoro-2-propanethiol | 12 |
| Hexafluoro-Chloro-propane | 10 |
| Chloro-tetrafluoro-Propene | 10 |
| Unknown | 3 |
| Chloro-trifluoro-propene isomer | 12 |
| 1,1,1,3,3,3-Hexafluoropropane | 999910 |

Example 2

A second cylinder of HFC-236fa (1,1,1,3,3,3-hexafluoropropane) was obtained and the HFC was treated as in Example 1. The results are shown in Table 2.

TABLE 2

GC/MSD Analysis of HFC-236fa

| COMPOUND | Prior to Treatment (ppma) | After Treatment (ppma) |
| --- | --- | --- |
| Trichlorofluoromethane | 80 | 48 |
| C4 Olefin | 5 | 8 |
| 1,1-Dichloro-2,2-Difluoroethene | 10 | 17 |
| 2-Methyl-1-Pentane | 9 | — |
| 3-Methyl-1-Pentane | 3 | — |
| Pentafluoro-2-Chloro-Propene + Hexane | 176 | 53 |
| Pentafluoro-1-Propene | 63 | 38 |
| Tetrafluoroethane | — | 34 |
| 1,1,1,3,3,3-Hexafluoropropane | 999654 | 999802 |

Example 3

Ethylene was polymerized using the treated HFC-236fa from the first cylinder of Example 1 as a diluent. Chromium oxide was used as the polymerization catalyst, with dibutyl magnesium (DBM) being used as a scavenger. No comonomer was used. Polymerization was carried out at a reaction temperature of 103.3° C. for 49 minutes.

The reactor was purged with nitrogen and 0.3 mmoles of DBM were added, followed by 750 cc of the diluent. The reactor temperature was raised to 103.3° C., and ethylene gas was then added to raise the system pressure to approximately 415 psig. The catalyst was then flushed into the reactor with 250 ml of additional diluent to initiate the reaction. Immediately following catalyst addition, the reactor pressure was raised to 470 psig with ethylene.

During the reaction, the system temperature was maintained at 103.3° C. by means of an external cooling water control system, and the pressure was maintained at 470 psig by means of an ethylene make-up system. (As the ethylene was consumed by reaction, additional ethylene was added to the system automatically to hold the reactor pressure at 470 psig.) At the end of the reaction time, the reactor was vented to terminate the reaction. The reactor was then opened, and the polymer product collected for analysis. The results are summarized in Table 3.

Example 4

Ethylene was polymerized using the treated HFC-236fa from the second cylinder of Example 2 as a diluent. The polymerization was carried out as in Example 3, except that the reaction time was for 60 minutes. The results are summarized in Table 3.

TABLE 3

| Diluent Cylinder | Catalyst Added (mg) | Run Time (min.) | Polymer Product (g) | Productivity (g/g/hr) |
| --- | --- | --- | --- | --- |
| 1 | 160 | 49.3 | 148 | 1127 |
| 2 | 156 | 60.0 | 60.1 | 385 |

In the two reaction experiments of this example, all variables were held constant with the exception of the source of the diluent and the total time of the reaction. The slight change in the total reaction time would not result in the significant production rate difference between the two runs, since the only other variable changed between the two experiments was the source of the diluent and the associated impurities. It is apparent that the chlorine compound impurities in the second cylinder were the primary cause of the lower productivity (385 versus 1127 g/g/hr).

Example 5

A cylinder of HFC-245fa (1,1,1,3,3-pentafluoropropane) was obtained and the HFC was treated as in Example 1. The results are shown in Table 4.

TABLE 4

| COMPOUND | Prior to Treatment (ppma) | After Treatment (ppma) |
| --- | --- | --- |
| Trichloro-trifluoro-ethane | 275 | 258 |
| Tetrafluoropropene | 32 | 27 |
| Chlorotetrafluoro-propene | 9 | 8 |
| Chlorotrifluoro-propene | 2 | 2 |
| 1,1,1,3,3-Hexafluoropropane + Chloro-tetrafluoro-propene | 36 | 56 |
| Unknown | 5 | 3 |
| 1,1,1,3,3-pentafluoropropane | 999641 | 999646 |

Example 6

Ethylene was polymerized using the treated HFC-245fa of Example 5 as a component of the diluent. Chromium oxide was used as the polymerization catalyst, with dibutyl magnesium (DBM) being used as a scavenger. No comonomer was used. Polymerization was carried out at a reaction temperature of 107.8° C. for 60 minutes.

The reactor was purged with nitrogen and 0.1 mmoles of DBM were added, followed by 250 cc of HFC-245fa. 500 cc of isobutane were then added. The reactor temperature was raised to 107.8° C., and ethylene gas was added to raise the system pressure to approximately 415 psig. The catalyst (53 mg) was then flushed with 250 ml of additional isobutane to initiate the reaction. Immediately following the catalyst addition, the reactor pressure was raised to 470 psig with ethylene.

During the reaction, the system temperature was maintained at 107.8° C. by means of an external cooling water control system, and the pressure was maintained at 470 psig by means of an ethylene make-up system. (As the ethylene was consumed by reaction, additional ethylene was added to the system automatically to hold the reactor pressure at 470 psig.) At the end of the reaction time, the reactor was vented to terminate the reaction. The reactor was then opened, and the polymer product collected for analysis. The results are summarized in Table 5.

Example 7

Example 6 was repeated, except that 146 mg of catalyst was used. The results are summarized in Table 5.

TABLE 5

| Example | Catalyst Added (mg) | Run Time (min.) | Polymer Product (g) | Productivity (g/g/hr) |
| --- | --- | --- | --- | --- |
| 6 | 53 | 60 | 30.9 | 583 |
| 7 | 146 | 60 | 124.2 | 851 |

As shown in Table 5, the productivity increased when the total amount of chromium oxide was increased from 53 mg to 146 mg. This result was unexpected since it is well known that the productivity should not depend on the amount of catalyst used. Normally, the use of higher amounts of catalyst would be expected to produce proportionally more polymer, but at the same value of productivity. The fact that the productivity was not constant in these tests indicates that the reaction was affected by chlorine compound impurities in the system. Since all feeds to the system (monomers and diluent) were the same in each experiment, and since the only known impurities were the chlorine containing compounds in the HFC diluent, the results indicate that the reaction was affected by the presence of chlorine containing impurities in the HFC.

The results also indicate that the effect of the chlorine containing impurities in the diluent was to deactivate a certain amount of the catalyst in each experiment. The actual amount of catalyst that was deactivated can be estimated from the results in Table 2. If it is assumed that the quantity of impurity compounds added to the system was the same in each case (as expected with identical feed streams), the amount of catalyst deactivated by the impurities can be calculated as equal to 22.4 mg. If this amount of catalyst were to be subtracted from the actual amounts of catalyst used in Table 2, the resulting productivity would have been the same in both cases, 1009 g/g/hr.

These results further indicate that the chromium oxide catalyst acts as an effective scavenger for the chlorine containing impurities, and demonstrate that the catalyst can be used to reduce the high concentration of chlorine containing hydrocarbon in the HFC. The additional catalyst present in the system, beyond that required to scavenge the impurities, can act as a conventional polymerization catalyst. The scavenging of impurities by the chromium oxide catalyst can take place in the same vessel or, alternatively, two vessels can be used such that the first vessel would act primarily as a chlorine reduction vessel and the second vessel as a conventional polymerization reactor.

Example 8

To demonstrate the effect of chlorine containing hydrocarbon on polymer productivity, trichlorofluoromethane (CFC-11), which was considered a contaminant in Example 2, was added to an ethylene polymerization system in isobutane, using the isobutane as a diluent. Ethylene copolymerization was carried out in a 2 L Zipperclave reactor. The reactor was first purged under a nitrogen flow for 2 hrs at 120-140° C. Then, 1.0 M AlEt$_3$ solution in hexanes, CFCl$_3$ solution in hexane, comonomer (1-butene or 1-hexene) and 850 mL of isobutane were added. Stirring was initiated. The reactor was heated to 85° C. and hydrogen was added. Finally, the reactor was pressurized with ethylene to a total pressure of 300-350 psig and catalyst was charged to the reactor by addition of the remaining 150 mL of isobutane. During polymerization, the reactor temperature was controlled via thermocouples in the reactor and the external jacket. Ethylene was fed on demand to maintain the desired total pressure. The polymerization was terminated after 45 min by stopping heating and venting the volatiles. The results are summarized in Table 6.

Catalyst A used in these experiments was a bulky ligand metallocene-type catalyst. More specifically, Catalyst A is a dimethylsilylbis(tetrahydroindenyl)zirconium dichloride (Me$_2$Si(H$_4$Ind)$_2$ZrCl$_2$) available from Albemarle Corporation, Baton Rouge, La. The (Me$_2$Si(H$_4$Ind)$_2$ZrCl$_2$) catalyst compound was combined with a 30 weight percent methylaluminoxane (MAO) in toluene (available from Albemarle, Baton Rouge, La.) is added. The catalyst was supported on Crosfield ES-70 grade silica dehydrated at 600° C. having approximately 1.0 weight percent water Loss on Ignition (LOI), with LOI being generally measured by determining the weight loss of the support material which has been heated and held at a temperature of about 1000° C. for about 22 hours. The Crosfield ES-70 grade silica has an average particle size of 40 microns, and is available from Crosfield Limited, Warrington, England.

Catalyst B used in these experiments was a bulky ligand metallocene-type catalyst made as follows. Into a 2 gallon (7.57 liters) reactor was charged first with 2.0 liters of toluene then, 1060 g of 30 wt % methylalumoxane solution in toluene (available from Albermarle, Baton Rouge, La.), followed by 23.1 g of bis(1,3-methyl-n-butyl cyclopentadienyl)zirconium dichloride as a 10% solution in toluene. The mixture was stirred for 60 minutes at room temperature after which 850 g of silica (Davison 948 dehydrated at 600° C. available from W.R. Grace, Davison Chemical Division, Baltimore, Md.) was added to the liquid with slow agitation. Stirring speed was increased for approximately 10 minutes to insure dispersion of the silica into the liquid and then appropriate amount of toluene was added to make up a slurry of liquid to solid having a consistency of 4 cc/g of silica. Mixing was continued for 15 minutes at 120 rpm after which 6 g of Kenamine AS-990 (available Witco Corporation, Memphis, Tenn.) was dissolved in 100 cc of toluene and was added and stirred for 15 minutes. Drying was then initiated by vacuum and some nitrogen purge at 175° F. (79.4° C.). When the polymerization catalyst comprising the carrier, silica, appeared to be free flowing, it was cooled down and discharged into a nitrogen purged vessel. An approximate yield of 1 Kg of dry polymerization catalyst was obtained due to some loses due to drying.

Catalyst C used in these experiments was a transition metal catalyst prepared from a mixture of $MgCl_2$, $TiCl_3 \cdot \frac{1}{3}AlCl_3$, and tetrahydrofuran (THF). The catalyst was supported on silica that was dehydrated at 600° C. A detailed description of the preparation procedure can be found in U.S. Pat. No. 4,710,537, which is herein incorporated by reference. The specific catalyst formulation used had a TNHAL/THF mole ration of 0.27 and a DEAC/THF mole ratio of 0.50 where TNHAL is tri-n-hexyl aluminum and DEAC is diethyl aluminum chloride.

TABLE 6

| Catalyst | $CFCl_3$ in Hexane | Comonomer Type | Comonomer Amount (ml) | Productivity (g/g/hr) |
|---|---|---|---|---|
| A | 0 | 1-Hexene | 20 | 1165 |
| A | 15 µmol/3.0 mL | 1-Hexene | 20 | 1317 |
| A | 83 µmol/0.5 mL | 1-Hexene | 20 | 524 |
| A | 500 µmol/3.0 mL | 1-Hexene | 20 | 181 |
| B | 0 | 1-Hexene | 60 | 1309 |
| B | 500 µmol/3.0 mL | 1-Hexene | 60 | 871 |
| C | 0 | 1-Butene | 60 | 539 |
| C | 500 µmol/3.0 mL | 1-Butene | 60 | 361 |

The data of Table 6 show that adding $CFCl_3$ with an amount similar to that found in HFC-236fa of Example 2 reduces catalyst activity by 33-84%.

Additional Examples

A series of absorption experimental runs were conducted in a simple, lab-scale column to determine the absorption capacity of two different types of activated carbon obtained from a vendor. The absorption capacities were measured with both types of activated carbon using three different types of hydrofluorocarbon (HFC-134a, HFC-236fa, and HFC-245fa). Results of these experiments are shown in Tables I and II.

The absorption column was a ½ inch (1.27 cm) OD stainless steel tubing with valves fitted on either side. The ½ inch (1.27 cm) stainless steel tubing was 9⅞ inches long (25.1 cm) with an internal diameter of 0.430 inch (10.9 mm). The column was packed with one of two types of activated carbon obtained from Calgon Carbon Corporation. The first sample was described by the vendor as "Calgon Activated Carbon, Type AP4-60." The second was described as "Calgon Activated Carbon, Type OVC Plus 4X6." The AP4-60 activated carbon was in the form of cylindrically shaped pellets, while the OVC Plus material was in the form of flakes. Both of these carbons were crushed with a mortar and pestle to a smaller size to fit inside the absorption column. The crushing reduced the average size of the particles or flakes to approximately 25 to 50 percent of their original size, with some fines. Glass wool packing was inserted on both ends of the column (next to the valves) to prevent any carbon from entering in to the valve areas. The HFC-245fa was obtained from Honeywell, as marketed under their trade name Enovate 3000. The HFC-236fa was obtained from DuPont, marketed as SUVA 236fa. The HFC-134a was an automotive grade material, marketed as R-134a. These materials were used as received without purification.

The fluorocarbon was allowed to vaporize or boil from its holding container through a line that led to the bottom of the absorption column. Between the column and the HFC source were two rotameters (flow indicating devices). Each rotameter had a flow range of 50 ml/min of air at 21.1° C. at atmospheric pressure. The rotameters were arranged in parallel to provide a flow range of 100 ml/min of air at atmospheric pressure. (The actual flow range of the rotameter depends on the Mw of the gas. For a gas of known Mw, the actual flow rate can be obtained from the indicated flow rate using methods that are well known in the art.) On the exit side of the absorption column, a ¼ inch (0.64 cm) line was directed down to a coil of stainless steel tubing that was contained within a beaker of dry ice. The chilled coil of stainless steel tubing acted as a condenser to liquefy (and detect) fluorocarbon gas coming from the absorption column. The downstream end of the condenser coil was vented to the atmosphere within a fume hood. Prior to each run, the weight of the empty column (with glass wool and valves) was weighed and recorded as the tare weight. The column was weighed again after the addition of activated carbon. The column was then connected to the feed and exit lines, and fluorocarbon (as a gas) was passed through the adsorption column. The flow rate of fluorocarbon was set at an indicated 25 to 30 ml/min on each rotameter. Initially there was no fluorocarbon condensed in the coil, indicating that the fluorocarbon was being adsorbed by the activated carbon in the column. Flow through the column was continued until some liquid began to "spit" out of the end of the condenser. This indicated that fluorocarbon was no longer being adsorbed by the column, and the limiting adsorption capacity had been reached. The flow of fluorocarbon gas was allowed to continue one more minute to ensure complete saturation, and the flow was then stopped. The valves on either side of the absorption column were closed and then the column removed and weighed. The increase in weight of the absorption column was taken as the weight of fluorocarbon adsorbed. Upon the completion of the run, the valves were removed and the activated carbon was poured out to prepare for the next test. No gas release was observed when opening or removing the valves, indicating that the fluorocarbon initially adsorbed during the tests remained adsorbed on the activated carbon.

TABLE I

Activated Carbon Absorption Results With Fluorocarbon (FC)

| Activated Carbon Type | FC Type | FC Mw (g/mole) | Wt. Empty Tube, w/valves (g) | Wt. of Tube w/Carbon (g) |
|---|---|---|---|---|
| AP4-60 | HFC-245fa | 134 | 394.30 | 406.42 |
| AP4-60 | R-134a | 102 | 394.45 | 406.74 |
| AP4-60 | HFC-236fa | 152 | 394.41 | 407.14 |
| OVC Plus | HFC-236fa | 152 | 394.46 | 405.10 |
| OVC Plus | R-134a | 102 | 394.44 | 405.68 |
| OVC Plus | HFC-245fa | 134 | 394.45 | 405.65 |

TABLE II

| Activated Carbon Type | Wt. Carbon (g) | Wt. of Tube w/Carbon & FC (g) | Wt. of FC Absorbed (g) | FC/C Ratio by Weight | FC/C Molar Ratio |
|---|---|---|---|---|---|
| AP4-60 | 12.12 | 412.75 | 6.33 | 0.522 | 0.0468 |
| AP4-60 | 12.29 | 410.93 | 4.19 | 0.341 | 0.0401 |
| AP4-60 | 12.73 | 413.81 | 6.67 | 0.524 | 0.0414 |
| OVC Plus | 10.64 | 411.39 | 6.29 | 0.591 | 0.0467 |
| OVC Plus | 11.24 | 410.92 | 5.24 | 0.466 | 0.0549 |
| OVC Plus | 11.20 | 412.39 | 6.74 | 0.602 | 0.0539 |

The above tests indicate that the activated carbon materials had surprisingly high adsorption capacities of between 34 to 60 percent of fluorocarbons by weight as indicated in Tables I and II. Thus in a preferred embodiment, the vent streams from a process could be purified (i.e. fluorocarbon removed) with reduced amounts of activated carbon than would normally be used in an activated carbon bed in a hydrocarbon process.

Having now fully described this invention, it will be appreciated by those skilled in the art that the invention can be performed within a wide range of parameters within what is claimed, without departing from the spirit and scope of the invention. All documents described herein are incorporated by reference herein, including any priority documents and/or testing procedures. Likewise, the term "comprising" is considered synonymous with the term "including" for purposes of Australian law.

The invention claimed is:

1. A polymerization process, comprising mixing together a catalyst system, at least one olefin monomer and a hydrofluorocarbon diluent to produce a polymer, wherein the mixture in which the polymer is produced contains no single chlorine containing hydrocarbon compound at greater than 40 ppma, wherein at least 5 volume percent of the hydrofluorocarbon is present based on the total volume of the diluent in the mixture, and wherein the monomers to be polymerized are not fluoromonomers.

2. The process of claim 1, wherein the mixture in which the polymer is produced contains no single chlorine containing hydrocarbon compound at greater than 30 ppma.

3. The process of claim 2, wherein the mixture in which the polymer is produced contains no single chlorine containing hydrocarbon compound at greater than 25 ppma.

4. The process of claim 3, wherein the mixture in which the polymer is produced contains no single chlorine containing hydrocarbon compound at greater than 20 ppma.

5. The process of claim 1, wherein the polymerization is carried out at a productivity of at least 400 g/g/hr.

6. The process of claim 5, wherein the polymerization is carried out at a productivity of at least 500 g/g/hr.

7. The process of claim 6, wherein the polymerization is carried out at a productivity of at least 600 g/g/hr.

8. The process of claim 7, wherein the polymerization is carried out at a productivity of at least 700 g/g/hr.

9. The process of claim 8, wherein the polymerization is carried out at a productivity of at least 800 g/g/hr.

10. The process of claim 1, wherein the polymerization is carried out at a fouling of not greater than 5 wt %.

11. The process of claim 10, wherein the polymerization is carried out at a fouling of not greater than 4 wt %.

12. The process of claim 11, wherein the polymerization is carried out at a fouling of not greater than 3 wt %.

13. The process of claim 12, wherein the polymerization is carried out at a fouling of not greater than 2 wt %.

14. The process of claim 13, wherein the polymerization is carried out at a fouling of not greater than 1 wt %.

15. The process of claim 1, wherein the hydrofluorocarbon is represented by the formula:

$$C_xH_yF_z$$

wherein x is an integer from 1 to 40, y is greater than or equal to 0, and z is an integer and at least one.

16. The process of claim 1, wherein the at least one monomer includes one or more of ethylene, propylene, butene-1, pentene-1,4-methyl-pentene-1, hexene-1, octene-1, decene-1,3-methyl-pentene-1, norbornene, norbornadiene, 3,5,5-trimethyl-1-hexene, 5-ethyl-1-nonene, vinyl norbornene, and ethylidene monomers.

17. The process of claim 1, wherein the chlorine containing hydrocarbon compound includes one or more compounds represented by the formula:

$$Cl_aF_bC_cH_d$$

wherein a is an integer of from 1 to 14, b is an integer of from 1 to 13, c is an integer of from 1 to 6, and d is an integer of from 0 to 13.

18. The process of claim 1, wherein the chlorine containing hydrocarbon compound is selected from the group consisting of: trichlorofluoromethane, hexafluorochloropropane, chlorotetrafluoropropene, chlorotrifluoropropene, 1,1-dichloro-2,2-difluoroethene, pentafluoro-2-chloropropene.

19. The process of claim 1, wherein the chlorine containing hydrocarbon compound is trichlorofluoromethane.

20. The process of claim 1, wherein one or more of the chlorine containing hydrocarbon compounds are removed from a mixture containing the hydrofluorocarbon prior to producing the polymer.

21. The process of claim 20, wherein the mixture contains a total amount of chlorine containing hydrocarbons of 50,000 ppm or less, by mass.

22. The process of claim 20, wherein the one or more chlorine containing compounds are removed by one or more processes selected from the group consisting of distillation, extractive distillation, contacting with metal permanganate, contacting with chromium oxide, adsorption, reactive distillation, and contacting with one or more decomposing agents.

23. A polymerization process, comprising:
a) removing chlorine containing hydrocarbons from a mixture containing hydrofluorocarbon to produce a hydrofluorocarbon product containing no single chlorine containing hydrocarbon compound above 40 ppma, and
b) mixing the hydrofluorocarbon product with at least one olefin monomer and a catalyst system to produce a polymer, wherein the mixture in which the polymer is produced comprises at least 5 volume percent of the hydrofluorocarbon product, and the monomers to be polymerized are not fluoromonomers.

24. The process of claim 23, wherein the mixture in which the polymer is produced contains no single chlorine containing hydrocarbon compound at greater than 30 ppma.

25. The process of claim 24, wherein the mixture in which the polymer is produced contains no single chlorine containing hydrocarbon compound at greater than 25 ppma.

26. The process of claim 23, wherein the mixture in which the polymer is produced contains no single chlorine containing hydrocarbon compound at greater than 20 ppma.

27. The process of claim 23, wherein the polymerization is carried out at a productivity of at least 400 g/g/hr.

28. The process of claim 27, wherein the polymerization is carried out at a productivity of at least 500 g/g/hr.

29. The process of claim 28, wherein the polymerization is carried out at a productivity of at least 600 g/g/hr.

30. The process of claim 29, wherein the polymerization is carried out at a productivity of at least 700 g/g/hr.

31. The process of claim 30, wherein the polymerization is carried out at a productivity of at least 800 g/g/hr.

32. The process of claim 23, wherein the polymerization is carried out at a fouling of not greater than 5 wt %.

33. The process of claim 32, wherein the polymerization is carried out at a fouling of not greater than 4 wt %.

34. The process of claim 33, wherein the polymerization is carried out at a fouling of not greater than 3 wt %.

35. The process of claim 34, wherein the polymerization is carried out at a fouling of not greater than 2 wt %.

36. The process of claim 35, wherein the polymerization is carried out at a fouling of not greater than 1 wt %.

37. The process of claim 23, wherein the hydrofluorocarbon is represented by the formula:

$$C_xH_yF_z$$

wherein x is an integer from 1 to 40, y is greater than or equal to 0, and z is an integer and at least one.

38. The process of claim 23, wherein the at least one monomomer includes one or more of ethylene, propylene, butene-1, pentene-1,4-methyl-pentene-1, hexene-1, octene-1, decene-1, 3-methyl-pentene-1, norbornene, norbornadiene, 3,5,5-trimethyl-1-hexene, 5-ethyl-1-nonene, vinyl norbornene, and ethylidene monomers.

39. The process of claim 23, wherein the chlorine containing hydrocarbon compound includes one or more compounds represented by the formula:

$$Cl_aF_bC_cH_d$$

wherein a is an integer of from 1 to 14, b is an integer of from 1 to 13, c is an integer of from 1 to 6, and d is an integer of from 0 to 13.

40. The process of claim 23, wherein the chlorine containing hydrocarbon compound is selected from the group consisting of: trichlorofluoromethane, hexafluorochloropropane, chlorotetrafluoropropene, chlorotrifluoropropene, 1,1-dichloro-2,2-difluoroethene, pentafluoro-2-chloropropene.

41. The process of claim 23, wherein the chlorine containing hydrocarbon compound is trichlorofluoromethane.

42. The process of claim 23, wherein the mixture contains a total amount of chlorine containing hydrocarbons of 50,000 ppm or less, by mass.

43. The process of claim 23, wherein the one or more chlorine containing compounds are removed by one or more processes selected from the group consisting of distillation, extractive distillation, contacting with metal permanganate, contacting with chromium oxide, adsorption, reactive distillation, and contacting with one or more decomposing agents.

* * * * *